US011635444B2

(12) United States Patent
Yaita

(10) Patent No.: US 11,635,444 B2
(45) Date of Patent: Apr. 25, 2023

(54) AUTOMATIC ANALYZER AND PROGRAM

(71) Applicant: JEOL Ltd., Tokyo (JP)

(72) Inventor: Tsuyoshi Yaita, Tokyo (JP)

(73) Assignee: JEOL Ltd., Tokyo (JP)

( * ) Notice: Subject to any disclaimer, the term of this patent is extended or adjusted under 35 U.S.C. 154(b) by 642 days.

(21) Appl. No.: 16/737,233

(22) Filed: Jan. 8, 2020

(65) Prior Publication Data

US 2020/0217867 A1 Jul. 9, 2020

(30) Foreign Application Priority Data

Jan. 9, 2019 (JP) .............................. JP2019-001577

(51) Int. Cl.
*G01N 35/10* (2006.01)
*G01N 33/50* (2006.01)

(52) U.S. Cl.
CPC ......... *G01N 35/1011* (2013.01); *G01N 33/50* (2013.01); *G01N 2035/1013* (2013.01); *G01N 2035/1025* (2013.01)

(58) Field of Classification Search
None
See application file for complete search history.

(56) References Cited

U.S. PATENT DOCUMENTS

| 4,818,492 A * | 4/1989 | Shimizu | G01F 23/263 73/863.02 |
| 4,864,856 A * | 9/1989 | Ichikawa | G01F 23/2967 73/864.34 |
| 5,319,954 A * | 6/1994 | Koeda | G01N 35/1016 73/19.1 |
| 5,646,049 A * | 7/1997 | Tayi | B01L 3/08 436/805 |
| 5,843,378 A * | 12/1998 | El-Hage | G01N 35/1009 422/63 |
| 10,690,691 B2 * | 6/2020 | Yaita | G01N 35/1011 |
| 2006/0207322 A1 * | 9/2006 | Krufka | G01F 25/24 73/304 C |
| 2007/0020763 A1 * | 1/2007 | Ingenhoven | G01N 1/14 436/43 |

(Continued)

FOREIGN PATENT DOCUMENTS

| CN | 103748471 A | 4/2014 |
| EP | 3276360 A1 | 1/2018 |

(Continued)

OTHER PUBLICATIONS

Extended European Search Report issued in EP19219670.7 dated May 27, 2020.

*Primary Examiner* — Brian R Gordon
(74) *Attorney, Agent, or Firm* — The Webb Law Firm

(57) ABSTRACT

A feature amount extraction unit outputs, as a data series, a feature amount of time-series data of an oscillation frequency of an AC signal of an oscillation circuit until a certain time elapses from when a dispensing probe starts to be lowered. Then, a bubble contact determination processing unit determines whether a liquid level has been normally detected based on a correlation between a waveform of the data series of the feature amount and an abnormal waveform model. Further, based on a determination result, a second controller determines a deviation between a tip portion of the dispensing probe and the liquid level in a container and a factor of the deviation.

4 Claims, 20 Drawing Sheets

(56) References Cited

U.S. PATENT DOCUMENTS

| | | | |
|---|---|---|---|
| 2007/0116600 A1* | 5/2007 | Kochar | B01L 3/5082 |
| | | | 422/65 |
| 2007/0144253 A1* | 6/2007 | Kobayashi | G01N 35/1011 |
| | | | 73/304 C |
| 2007/0240505 A1* | 10/2007 | Cammarata | G01F 23/284 |
| | | | 73/304 R |
| 2010/0332158 A1* | 12/2010 | Courtial | G01F 23/263 |
| | | | 702/55 |
| 2012/0000296 A1* | 1/2012 | Weng | G01N 35/1011 |
| | | | 73/863.02 |
| 2012/0114526 A1* | 5/2012 | Watanabe | G01N 35/1009 |
| | | | 422/63 |
| 2013/0132006 A1* | 5/2013 | Gwynn | B01L 3/021 |
| | | | 702/55 |
| 2013/0280143 A1* | 10/2013 | Zucchelli | G01N 35/026 |
| | | | 422/501 |
| 2014/0024133 A1* | 1/2014 | Carter, Jr | B01F 35/221 |
| | | | 436/174 |
| 2014/0220693 A1 | 8/2014 | Yamazaki et al. | |
| 2015/0268230 A1* | 9/2015 | Endo | G01F 23/268 |
| | | | 73/290 R |
| 2017/0138976 A1* | 5/2017 | Pawlowski | G01N 35/1016 |
| 2018/0031591 A1 | 2/2018 | Yaita | |
| 2022/0001673 A1* | 1/2022 | Anderson | B41J 2/17546 |
| 2022/0146540 A1* | 5/2022 | Noda | G01N 35/00594 |

FOREIGN PATENT DOCUMENTS

| | | |
|---|---|---|
| JP | 10206432 A | 8/1998 |
| JP | 11271323 A | 10/1999 |
| JP | 200428673 A | 1/2004 |
| JP | 201194985 A | 5/2011 |

\* cited by examiner

FIG. 6

| | BUBBLE CONTACT DETERMINATION | FIRST DETERMINATION | SECOND DETERMINATION | THIRD DETERMINATION | FOURTH DETERMINATION | LIQUID LEVEL DEVIATION DETERMINATION NORMAL OR ABNORMAL | FIRST CANDIDATE FOR DEVIATION FACTOR |
|---|---|---|---|---|---|---|---|
| PATTERN0 | Pass | Pass | Pass | Pass | Pass | NORMAL | N/A |
| PATTERN1 | Fail | Pass | Pass | Pass | Pass | ABNORMAL | BUBBLE |
| PATTERN2 | Pass | Pass | Pass | Pass | Fail | ABNORMAL | STATIC ELECTRICITY |
| PATTERN3 | Fail | Pass | Pass | Pass | Fail | ABNORMAL | STATIC ELECTRICITY |
| PATTERN4 | Pass | Pass | Pass | Fail | Pass | ABNORMAL | BUBBLE |
| PATTERN5 | Fail | Pass | Pass | Fail | Pass | ABNORMAL | BUBBLE |
| PATTERN6 | Pass | Pass | Pass | Fail | Fail | ABNORMAL | STATIC ELECTRICITY |
| PATTERN7 | Fail | Pass | Pass | Fail | Fail | ABNORMAL | STATIC ELECTRICITY |
| PATTERN8 | Pass | Pass | Fail | Pass | Pass | ABNORMAL | CONTACT |
| PATTERN9 | Fail | Pass | Fail | Pass | Pass | ABNORMAL | CONTACT |
| PATTERN10 | Pass | Pass | Fail | Pass | Fail | ABNORMAL | UNCLEAR |
| PATTERN11 | Fail | Pass | Fail | Pass | Fail | ABNORMAL | BUBBLE |
| PATTERN12 | Pass | Pass | Fail | Fail | Pass | ABNORMAL | UNCLEAR |
| PATTERN13 | Fail | Pass | Fail | Fail | Pass | ABNORMAL | BUBBLE |
| PATTERN14 | Pass | Pass | Fail | Fail | Fail | ABNORMAL | UNCLEAR |
| PATTERN15 | Fail | Pass | Fail | Fail | Fail | ABNORMAL | BUBBLE |
| PATTERN16 | Pass | Fail | Pass | Pass | Pass | ABNORMAL | BUBBLE |
| PATTERN17 | Fail | Fail | Pass | Pass | Pass | ABNORMAL | BUBBLE |
| PATTERN18 | Pass | Fail | Pass | Pass | Fail | ABNORMAL | UNCLEAR |
| PATTERN19 | Fail | Fail | Pass | Pass | Fail | ABNORMAL | BUBBLE |
| PATTERN20 | Pass | Fail | Pass | Fail | Pass | ABNORMAL | BUBBLE |
| PATTERN21 | Fail | Fail | Pass | Fail | Pass | ABNORMAL | BUBBLE |
| PATTERN22 | Pass | Fail | Pass | Fail | Fail | ABNORMAL | STATIC ELECTRICITY |
| PATTERN23 | Fail | Fail | Pass | Fail | Fail | ABNORMAL | STATIC ELECTRICITY |
| PATTERN24 | Pass | Fail | Fail | Pass | Pass | ABNORMAL | CONTACT |
| PATTERN25 | Fail | Fail | Fail | Pass | Pass | ABNORMAL | CONTACT |
| PATTERN26 | Pass | Fail | Fail | Pass | Fail | ABNORMAL | STATIC ELECTRICITY |
| PATTERN27 | Fail | Fail | Fail | Pass | Fail | ABNORMAL | STATIC ELECTRICITY |
| PATTERN28 | Pass | Fail | Fail | Fail | Pass | ABNORMAL | CONTACT |
| PATTERN29 | Fail | Fail | Fail | Fail | Pass | ABNORMAL | CONTACT |
| PATTERN30 | Pass | Fail | Fail | Fail | Fail | ABNORMAL | STATIC ELECTRICITY |
| PATTERN31 | Fail | Fail | Fail | Fail | Fail | ABNORMAL | STATIC ELECTRICITY |

FIG. 7

| DEVIATION FACTOR DETERMINATION RESULT | RECOMMENDED COPING PROCEDURE DISPLAYED ON MONITOR |
|---|---|
| CONTACT | CHECK IF CONTAINER IS SET CORRECTLY<br>IF SAMPLE VOLUME IS SMALL,<br>TRANSFER SAMPLE TO SMALL-CAPACITY CONTAINER. |
| BUBBLE | REMOVE BUBBLES ON SAMPLE SURFACE |
| STATIC ELECTRICITY | WIPE SAMPLE CONTAINER WITH DAMP CLOTH |
| UNCLEAR | CHECK FOR CONTACT, BUBBLE AND STATIC ELECTRICITY |

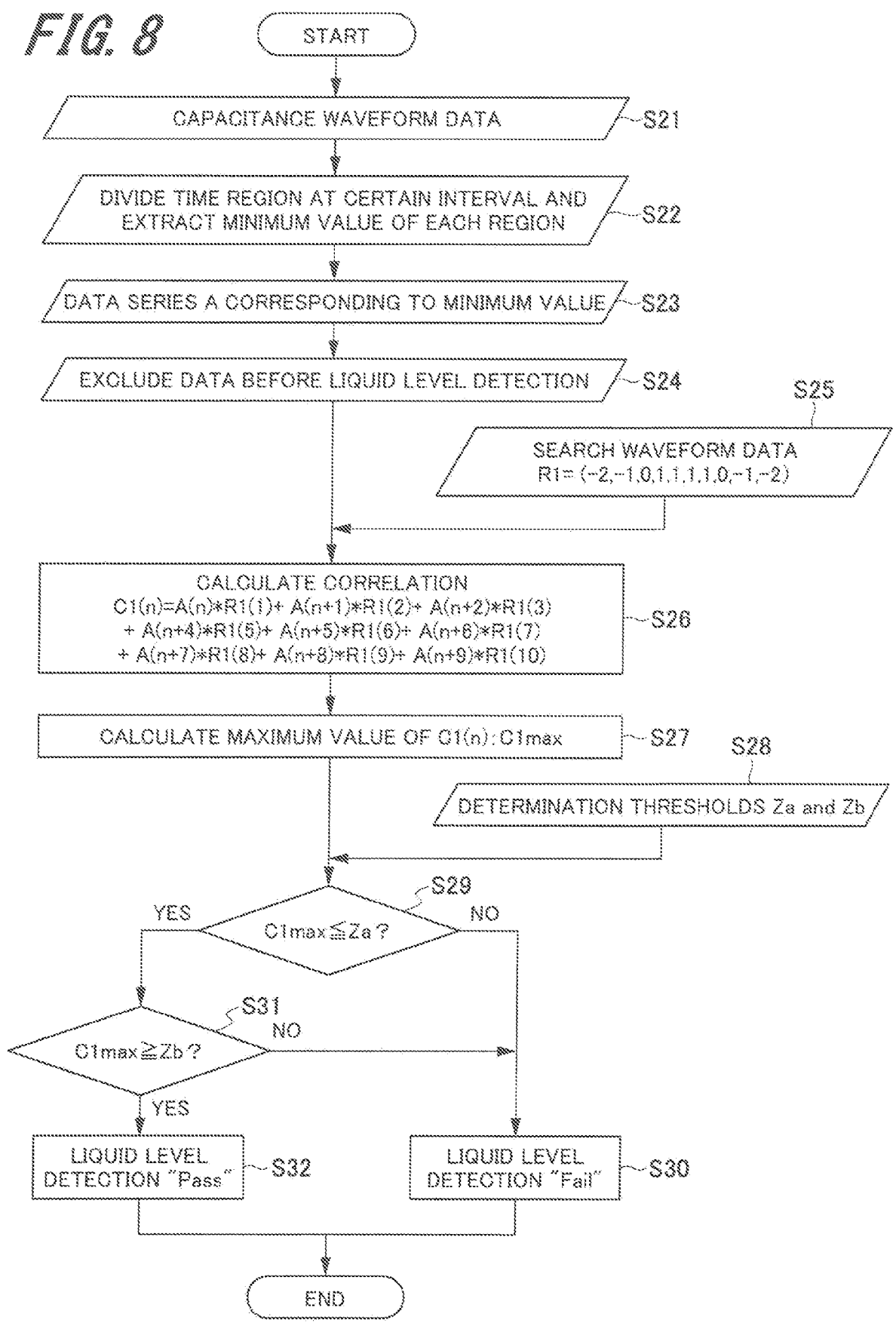

AUTOMATIC ANALYZER AND PROGRAM

CROSS-REFERENCE TO RELATED APPLICATION

This application claims priority to Japanese Patent Application No. 2019-001577 filed Jan. 9, 2019, the disclosure of which is hereby incorporated by reference in its entirety.

BACKGROUND

Field of the Invention

The present invention relates to an automatic analyzer and a program, and more particularly to a technology for detecting an erroneous detection of a tip portion of a dispensing probe on a surface of a liquid (hereinafter referred to as a "liquid level") in a container.

Description of Related Art

An automatic analyzer for clinical tests is used for tests in various fields such as biochemical tests, immunological tests, and blood transfusion tests. In such an automatic analyzer, a container for storing a sample or a reagent is disposed at a predetermined position on the analyzer. The automatic analyzer uses a dispensing mechanism including a dispensing probe and a pump connected to the dispensing probe to transport a liquid (sample and reagent) contained in a container thereof while sucking and holding the liquid, and then discharges the liquid into a target container (a reaction container, etc.).

In this dispensing mechanism, it is desirable to stop the dispensing probe at a liquid level to avoid contamination of the dispensing probe and the liquid. A capacitance method is widely used at present as a method for detecting a liquid level position.

The capacitance method is a method of monitoring a capacitance between a suction portion (tip portion) of the dispensing probe and a peripheral portion (for example, a ground of a device housing) and detecting a change. When the tip portion of the dispensing probe comes into contact with the liquid of the sample, etc., a capacitance value changes. Thus, when the change is detected using a threshold value, etc., it is possible to identify whether the dispensing probe is in contact with the liquid level or in the air. Normally, the capacitance is monitored when the dispensing probe is lowered into the container. When the capacitance greatly changes beyond a threshold, lowering of the dispensing probe is stopped at this time. In this way, the dispensing probe can be held in a state in which only the tip portion of the dispensing probe comes into contact with the liquid level.

As a specific example of the capacitance method, for example, in addition to a method of configuring a CR oscillation circuit shown in JP 11-271323 A and obtaining a change in the capacitance C from a change in oscillation frequency (see JP 11-271323 A), a lot of similar or related methods have been devised (for example, see JP 10-206432 A, JP 2011-094985 A, and JP 2004-028673 A).

As a technical problem related to liquid level detection of a conventional capacitance method, there is an event (hereinafter referred to as "liquid level deviation") in which even though the liquid level of the sample, etc. and the tip of the dispensing probe are separated from each other, it is determined that the tip of the dispensing probe has reached the liquid level. At this time, since the dispensing probe is in the air, a target sample may not be sucked. Therefore, there is a risk that a value near zero is erroneously reported as the concentration of a target component of the target sample. One of main factors for detecting an incorrect liquid level is bubbles generated on the liquid surface.

A problem caused by bubbles is that the dispensing probe stops when the dispensing probe comes into contact with a surface of a liquid bubble. The inside of the bubble is air, and the dispensing probe sucks air. Neither Patent JP 11-271323 A nor JP 10-206432 A describes that it is determined that a factor of erroneous detection is a bubble. Technologies described in JP 2011-094985 A and JP 2004-028673 A are based on a height at which the liquid level is detected, and thus it is considered that the technologies are effective to some extent for detecting bubbles. On the other hand, it is considered that not only a change in a state of a bubble when the bubble comes into contact with the dispensing probe but also a change in capacitance have various variations, and thus determining from height information has a problem in terms of accuracy.

Further, in the method of determination based on the height of the liquid level described in JP 2011-094985 A and JP 2004-028673 A, a possibility of erroneous detection due to a factor other than bubbles may not be denied, and it is difficult to notify that a factor of erroneous detection is bubbles. Since there is a plurality of factors when a user is notified of a possibility of liquid level deviation of a sample, it is difficult for the user to determine a countermeasure. When a sample having a possibility of abnormality is reexamined, it takes a long time to make the determination, thereby causing a delay in inspection. This fact ultimately degrades a benefit to a patient waiting for a test result.

SUMMARY

The invention has been made in consideration of the above situation and the invention allows detection of erroneous detection of liquid level detection caused by bubbles generated on a liquid surface with higher accuracy.

An automatic analyzer of an aspect of the invention includes a dispensing portion that has a dispensing probe and is configured to move a tip portion of the dispensing probe to a liquid level in a container and suck and discharge a liquid, an oscillation circuit connected to the dispensing probe to output an AC signal of an oscillation frequency according to a capacitance between the tip portion of the dispensing probe and a peripheral portion, a detector that detects whether the tip portion of the dispensing probe has come into contact with the liquid level in the container based on the oscillation frequency of the AC signal output from the oscillation circuit, a first controller that controls an operation of the dispensing portion based on a detection result of the detector, a feature amount extraction unit that divides time-series data of the oscillation frequency of the AC signal output by the oscillation circuit until a certain time elapses after the dispensing probe starts to be lowered for each certain section, extracts a feature amount for each certain section, and outputs the extracted feature amount as a data series, a bubble contact determination processing unit that computes a correlation between a waveform of the data series of the feature amount output from the feature amount extraction unit and an abnormal waveform model based on a waveform observed when the tip portion of the dispensing probe comes into contact with a bubble on the liquid level in the container, and determines whether liquid level detection has been normally performed based on a result of computing the correlation, and a second controller that determines a deviation between the tip portion of the dispensing probe and the liquid level in the container and a factor of the deviation based on a determination result of the bubble contact determination processing unit.

According to at least one aspect of the invention, it is possible to detect erroneous detection of liquid level detection caused by bubbles generated on a liquid surface with higher accuracy based on a determination result of the bubble contact determination processing unit.

Problems, configurations, and effects other than those described above will be clarified by the following description of embodiments.

BRIEF DESCRIPTION OF DRAWINGS

FIG. 6 illustrates an example of a liquid level deviation and deviation factor determination table illustrating a combination of respective determination results of a bubble contact determination process and a first determination process to a fourth determination process and a deviation factor according to an embodiment of the invention;

FIG. 7 illustrates an example of a recommended coping procedure table in which a recommended coping procedure for a deviation factor determination result is registered according to an embodiment of the invention;

FIG. 8 is a flowchart illustrating an example of a procedure of a bubble contact determination process according to an embodiment of the invention;

DETAILED DESCRIPTION

Figure 1:
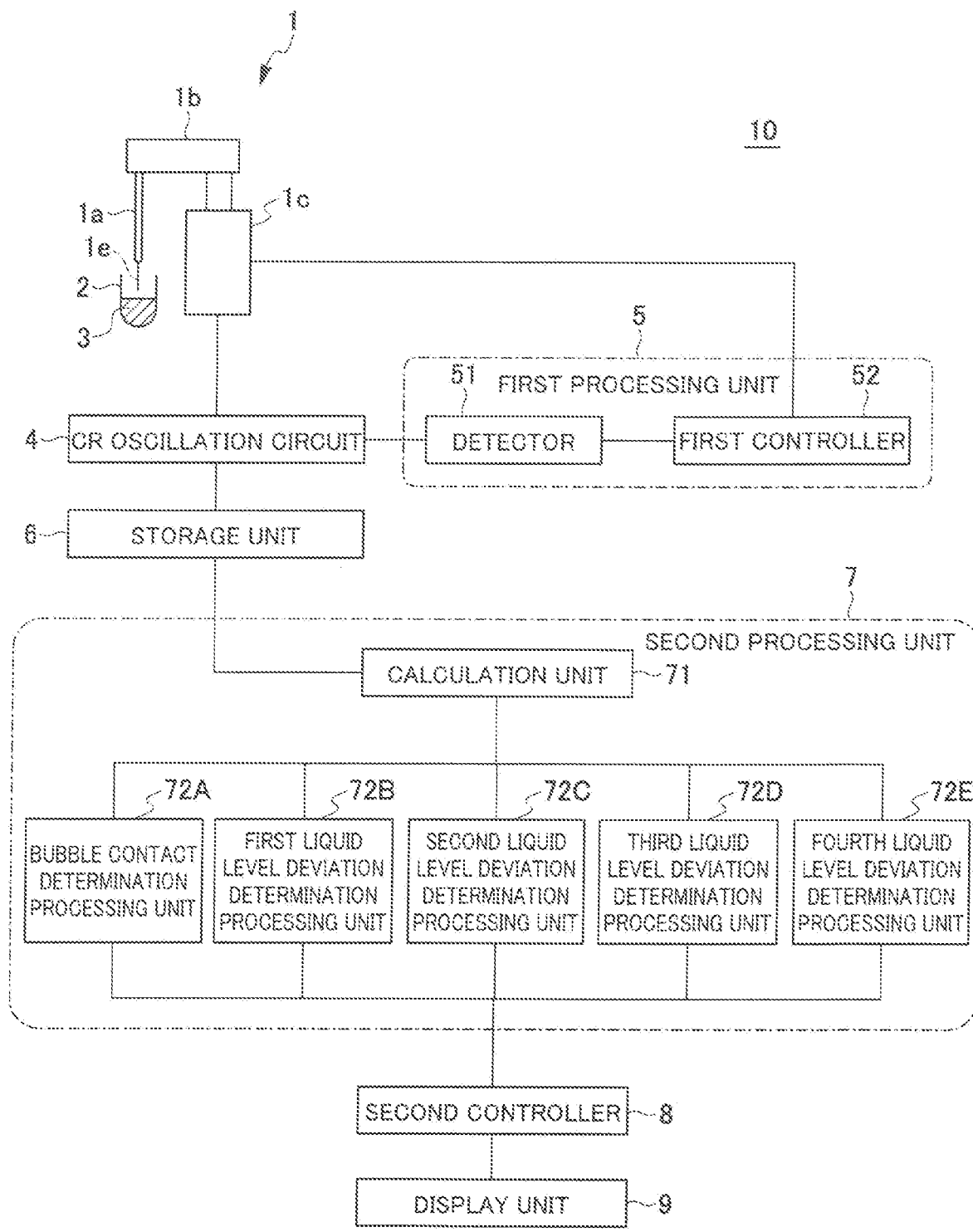
FIG. 1 is a block diagram illustrating a configuration example of an automatic analyzer according to an embodiment of the invention.

Hereinafter, an example of an embodiment for carrying out the invention will be described with reference to the accompanying drawings. In the respective drawings, a component having substantially the same function or configuration is denoted by the same reference numeral and redundant description is omitted.

<Overall Configuration of Automatic Analyzer>

FIG. 1 is a block diagram illustrating a configuration example of an automatic analyzer according to an embodiment.

The automatic analyzer 10 according to the present embodiment includes a mechanism for detecting a change in a capacitance value when a tip of a dispensing probe comes into contact with a liquid level by monitoring a capacitance between the dispensing probe that dispenses a liquid such as a sample or a reagent and a peripheral portion, and detecting a liquid level based on the detected change.

As illustrated in FIG. 1, the automatic analyzer 10 includes a dispensing unit 1, a CR oscillation circuit 4, a first processing unit 5, a storage unit 6, a second processing unit 7, a second controller 8, and a display unit 9.

The dispensing unit 1 (an example of a dispensing portion) includes a dispensing probe 1a, an arm 1b that holds the dispensing probe 1a, a drive mechanism 1c that drives the arm 1b, etc. The dispensing probe 1a is made of a conductive member such as a metal, and is hollow to accommodate a sucked liquid. An outer peripheral surface of the dispensing probe 1a is protected by a shield except for a tip portion 1e (suction portion) that sucks and discharges liquid.

The dispensing unit 1 is configured to be able to perform horizontal movement, vertical movement, and suck and discharge operations of the dispensing probe 1a using the drive mechanism 1c and the arm 1b. The drive mechanism 1c has a motor (not illustrated) that drives the arm 1b, for example. The dispensing unit 1 moves the tip portion 1e of the dispensing probe 1a to a liquid level of the sample 3 (an example of liquid) of the container 2 using the drive mechanism 1c and the arm 1b and sucks the sample 3. Then, the dispensing unit 1 transfers the dispensing probe 1a sucking the sample 3 to a target location (such as a reaction container), and discharges the sample 3. These operations of the dispensing unit 1 are controlled by the first processing unit 5 (first controller 52). The drive mechanism 1c is connected to the CR oscillation circuit 4 and the first processing unit 5.

The container 2 is transferred while being held by a holding member such as a turntable. The holding member is electrically grounded to a ground of a housing of the automatic analyzer 10 (hereinafter "device housing").

The CR oscillation circuit 4 (an example of an oscillation circuit) is a feedback oscillation circuit that performs feedback using a CR circuit including a resistor (R) and a capacitor (C), and generates a sine wave AC signal. The CR oscillation circuit 4 outputs an AC signal having an oscillation frequency corresponding to the capacitance between the tip portion 1e of the dispensing probe 1a and the peripheral portion (for example, the holding member, that is, the ground of the device housing). The CR oscillation circuit 4 has an analog-digital conversion circuit (not illustrated) and outputs a digital AC signal. In addition to the CR oscillation circuit, various other oscillation circuits such as an LC oscillation circuit can be applied to the oscillation circuit.

The first processing unit 5 includes a detector 51 and the first controller 52, analyzes an AC signal output from the CR oscillation circuit 4, and controls the dispensing unit 1 based on an analysis result.

The detector 51 is connected to the CR oscillation circuit 4 and monitors an oscillation frequency of the AC signal output from the CR oscillation circuit 4. That is, the detector 51 fetches the AC signal and detects the oscillation frequency of the AC signal at a predetermined sampling period. Then, the detector 51 detects whether the tip portion 1e of the dispensing probe 1a has come into contact with the liquid level in the container 2 based on the detected oscillation frequency, and outputs a signal indicating liquid level detection when the liquid level is detected.

The first controller 52 (first controller) outputs a control signal to the drive mechanism 1c of the dispensing unit 1 based on a detection result of the detector 51, and controls an operation of the dispensing probe 1a.

The storage unit 6 stores data of a digital AC signal output from the CR oscillation circuit 4 until a predetermined time elapses after the dispensing probe 1a starts to be lowered.

The second processing unit 7 performs a process of detecting whether there is an error in liquid level detection by the first processing unit 5. The second processing unit 7 includes a calculation unit 71, a bubble contact determination processing unit 72A, a first liquid level deviation determination processing unit 72B, a second liquid level deviation determination processing unit 72C, a third liquid level deviation determination processing unit 72D, and a fourth liquid level deviation determination processing unit 72E.

The calculation unit 71 (an example of a feature amount extraction unit) acquires time-series data (corresponding to a capacitance waveform) of the oscillation frequency of the AC signal from the data of the AC signal stored in the storage unit 6. Then, the feature amount is extracted from the time-series data of the oscillation frequency and output as a data series. For example, the feature amount is extracted for each certain section of the time-series data of the oscillation frequency.

The bubble contact determination processing unit 72A and the first liquid level deviation determination processing unit 72B to the fourth liquid level deviation determination processing unit 72E determines whether the liquid level of the container 2 has been normally detected using the data series of the feature amount output from the calculation unit 71. An outline of operations of the bubble contact determination processing unit 72A and the first liquid level deviation determination processing unit 72B to the fourth liquid level deviation determination processing unit 72E will be described below. Details of the respective determination processes will be described later with reference to FIG. 8, FIG. 14, FIG. 16, FIG. 18, and FIG. 20.

The bubble contact determination processing unit 72A computes a correlation between an abnormal waveform model and a waveform of data series of a feature amount (for example, a minimum value) for each certain section of time-series data of an oscillation frequency output from the calculation unit 71. Then, the bubble contact determination processing unit 72A determines whether the liquid level is normally detected from a result of computing the correlation, and outputs a determination result to the second controller 8. The abnormal waveform model is a waveform model based on a waveform characteristically observed when the tip portion 1e of the dispensing probe 1a comes into contact with a bubble on the liquid level in the container 2. In the bubble contact determination process by the calculation unit 71 and the bubble contact determination processing unit 72A, a shape of change in the waveform (capacitance waveform) by the time-series data of the oscillation frequency is observed.

The first liquid level deviation determination processing unit 72B (an example of a first determination processing unit) computes a correlation between a waveform of a data series of a differential value of a feature amount (for example, a minimum value) for each certain section of time-series data of an oscillation frequency output from the calculation unit 71 and the corresponding normal waveform. Then, the first liquid level deviation determination processing unit 72B determines whether the liquid level is normally detected from a computation result, and outputs a determination result to the second controller 8. In the first determination process by the calculation unit 71 and the first liquid level deviation determination processing unit 72B, a shape of change in the waveform (capacitance waveform) by the time-series data of the oscillation frequency is observed.

The second liquid level deviation determination processing unit 72C (an example of a second determination processing unit) compares a threshold with a maximum value of a data series of a differential value of a feature amount (for example, a minimum value) for each certain section of time-series data of an oscillation frequency output from the calculation unit 71. Then, the second liquid level deviation determination processing unit 72C determines whether the liquid level is normally detected from a comparison result, and outputs a determination result to the second controller 8. In the second determination process by the calculation unit 71 and the second liquid level deviation determination processing unit 72C, a magnitude (steepness) of change in the waveform (capacitance waveform) by the time-series data of the oscillation frequency is observed.

The third liquid level deviation determination processing unit 72D (an example of a third determination processing unit) computes a section in which a feature amount (for example, a minimum value) for each certain section extracted from time-series data of an oscillation frequency output from the calculation unit 71 satisfies a predetermined condition. Then, the third liquid level deviation determination processing unit 72D compares a length of the section with a threshold, determines whether the liquid level is normally detected from a comparison result, and outputs a determination result to the second controller 8. In the third determination process by the calculation unit 71 and the third liquid level deviation determination processing unit 72D, a shape the waveform (capacitance waveform) by the time-series data of the oscillation frequency is observed.

The fourth liquid level deviation determination processing unit 72E (an example of a fourth determination processing unit) computes a maximum value of each data series from the data series of the maximum value and the data series of the minimum value as feature amounts for each certain section extracted from the time-series data of the oscillation frequency output from the calculation unit 71. Then, the fourth liquid level deviation determination processing unit 72E compares a difference between maximum values of each data series with a threshold, determines whether the liquid level is normally detected from a comparison result, and outputs a determination result to the second controller 8. In the fourth determination process by the calculation unit 71 and the fourth liquid level deviation determination processing unit 72E, stability (presence or absence of noise, etc.) of the waveform (capacitance waveform) by the time-series data of the oscillation frequency is observed.

The second controller 8 determines a deviation between the tip portion 1e of the dispensing probe 1a and the liquid level in the container 2 and a factor of the deviation by combining the respective determination results of the bubble contact determination processing unit 72A and the first liquid level deviation determination processing unit 72B to the fourth liquid level deviation determination processing unit 72E. A determination result of the second controller 8 is output to the display unit 9 and displayed on the screen of the display unit 9. Determination of the liquid level deviation caused by the contact with the bubbles may be performed based only on the determination result by the bubble contact determination processing unit 72A.

<Hardware Configuration of Computer>

Figure 2:
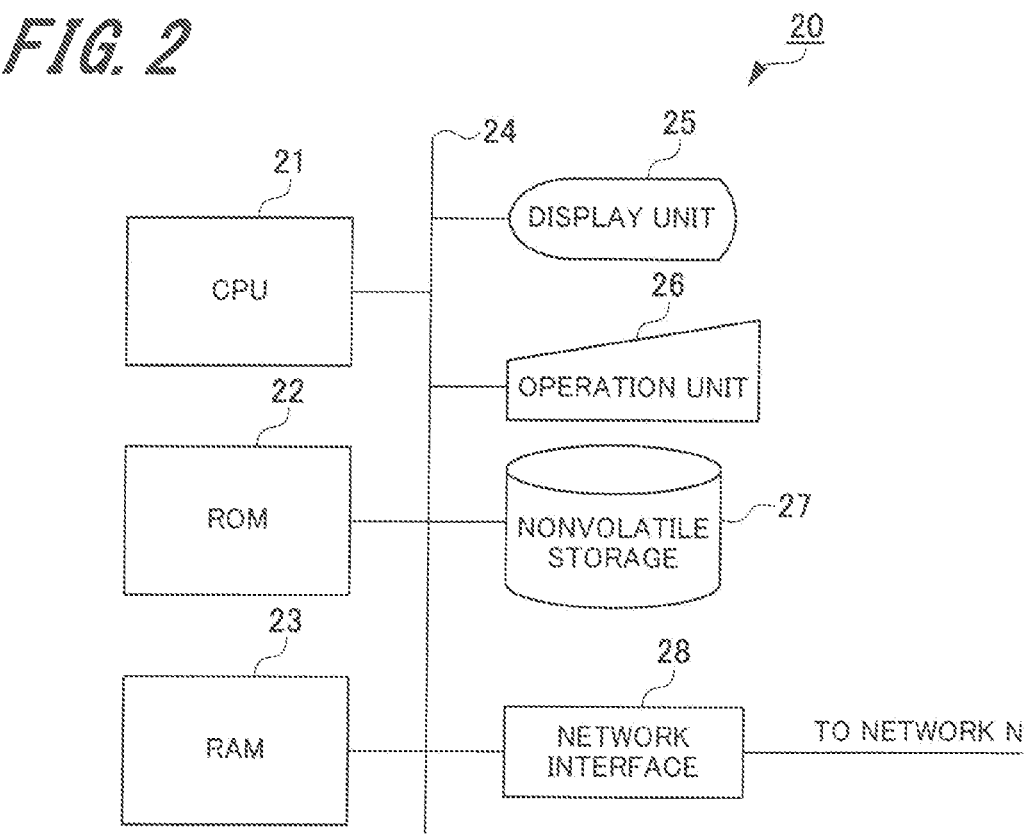
FIG. 2 is a block diagram illustrating a hardware configuration example of a computer included in the automatic analyzer according to an embodiment of the invention.

FIG. 2 is a block diagram illustrating a hardware configuration example of a computer included in the automatic analyzer 10.

The computer 20 includes a central processing unit (CPU) 21, a read only memory (ROM) 22, and a random access memory (RAM) 23, each of which is connected to a bus 24. Furthermore, the computer 20 includes a display unit 25, an operation unit 26, a nonvolatile storage 27, and a network interface 28.

The CPU 21 reads a program code of software that implements each function according to the present embodiment from the ROM 22 and executes the program code. For example, the respective functions of the first processing unit 5, the second processing unit 7, and the second controller 8 can be realized by the CPU 21. The computer 20 may include a processing device such as a micro-processing unit (MPU) instead of the CPU 21.

Variables, parameters, etc. generated during arithmetic processing are temporarily written to the RAM 23. For example, the RAM 23 may store data of a digital AC signal output from the CR oscillation circuit 4 as the storage unit 6 of FIG. 1.

The display unit 25 corresponds to the display unit 9 of FIG. 1 and displays a result of processing performed by the computer 20, etc. For example, the display unit 25 is a liquid crystal display monitor. For example, a keyboard, a mouse, a touch panel, etc. is used for the operation unit 26, and a user can perform predetermined operation inputs and instructions.

For example, a hard disk drive (HDD), a solid state drive (SSD), a flexible disk, an optical disc, a magneto-optical disc, a CD-ROM, a CD-R, a magnetic tape, a nonvolatile memory card, etc. is used as the nonvolatile storage 27. Besides an operating system (OS) and various parameters, a program for causing the computer 20 to function is recorded in the nonvolatile storage 27. For example, a program that defines a liquid level deviation determination and deviation factor determination process (see FIG. 5), a liquid level deviation and deviation factor determination table 41 (see FIG. 6), a recommended coping procedure table 42 (see FIG. 7), etc. are stored in the nonvolatile storage 27.

For example, a network interface card (NIC), etc. is used as the network interface 28, and various types of data can be transmitted and received between devices via a network N such as a LAN.

<Operation when Liquid Level is Detected>

Figure 3:
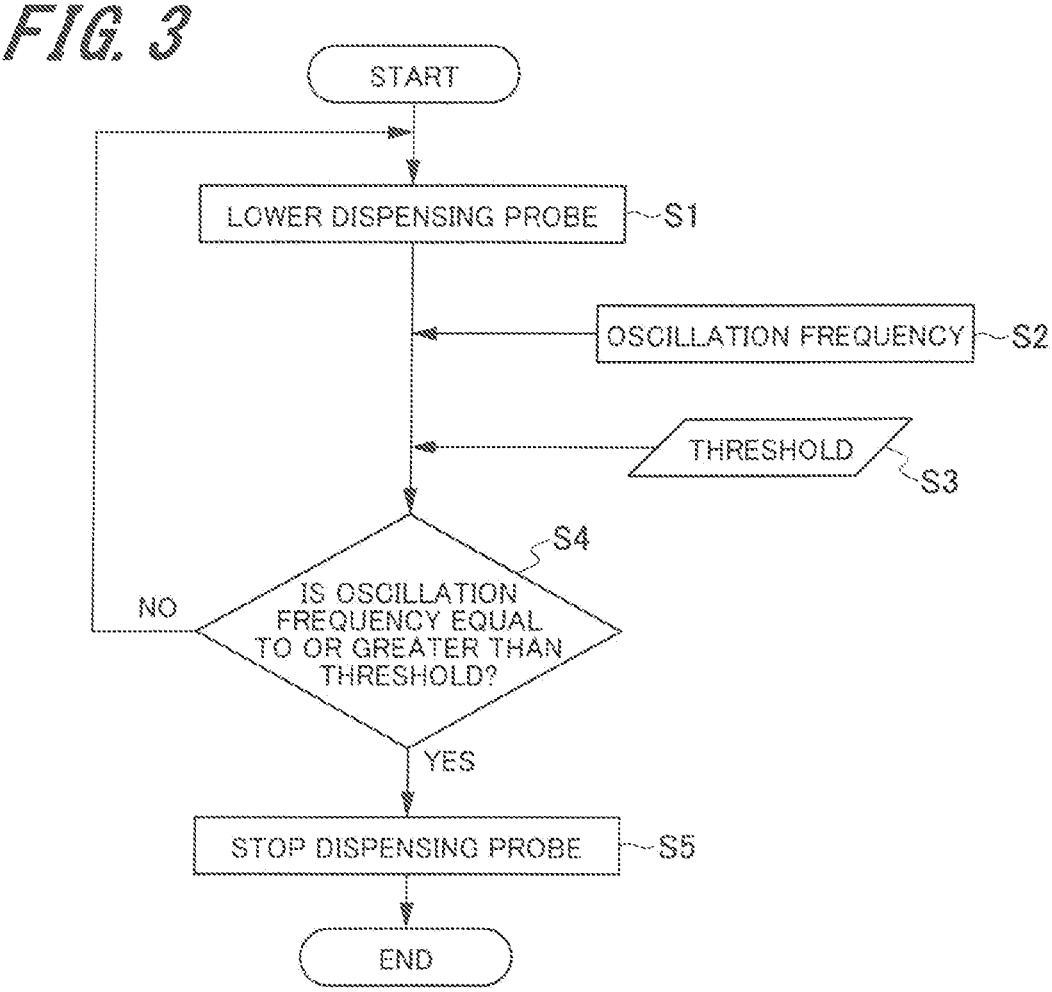
FIG. 3 is a flowchart illustrating an example of a procedure of an operation when a liquid level is detected by a first processing unit of the automatic analyzer according to an embodiment of the invention.

FIG. 3 is a flowchart illustrating an example of a procedure of an operation when a liquid level is detected by the first processing unit 5 of the automatic analyzer 10. This process is realized by the first processing unit 5, the dispensing unit 1, and the CR oscillation circuit 4 of FIG. 1.

As a premise, the detector 51 of the first processing unit 5 subsequently monitors the oscillation frequency of the AC signal output from the CR oscillation circuit 4. First, when the container 2 to be inspected is transported, the first controller 52 of the first processing unit 5 starts an operation of lowering the dispensing probe 1a at a set timing (step S1).

In this instance, monitoring of the oscillation frequency by the detector 51 is continued (step S2). In parallel with this monitoring, the detector 51 reads a threshold for the oscillation frequency preset in the storage unit 6 from the storage unit 6 (step S3). Then, the detector 51 determines whether the monitored oscillation frequency is equal to or greater than the threshold (step S4).

When the tip portion 1e of the dispensing probe 1a comes into contact with the liquid level in the container 2, the capacitance value between the dispensing probe 1a and the peripheral portion significantly increases, and thus the oscillation frequency exceeds the threshold. When it is determined that the oscillation frequency is equal to or greater than the threshold in step S4 (when step S4 corresponds to YES determination), the detector 51 outputs a signal indicating that the liquid level in the container 2 has been detected (liquid level detection ON signal) to the first controller 52. After receiving the liquid level detection ON signal, the first controller 52 immediately transmits a control signal for stopping lowering of the dispensing probe 1a to the drive mechanism 1c of the dispensing unit 1 (step S5). In this way, the drive mechanism 1c stops the operation of lowering the dispensing probe 1a. Then, the tip portion 1e of the dispensing probe 1a is in contact with the liquid level in the container 2.

On the other hand, when it is determined in step S4 that the oscillation frequency is less than the threshold (when step S4 corresponds to NO determination), the first controller 52 proceeds to step S1 and continues the operation of lowering the dispensing probe 1a.

The procedure of the liquid level detection operation performed through the first processing unit 5 described above uses conventional technology and is a premise of one embodiment of the invention. The procedure of the liquid level detection operation may be realized by either hardware or software.

<Waveform Example of Normal Capacitance>

Figure 4:
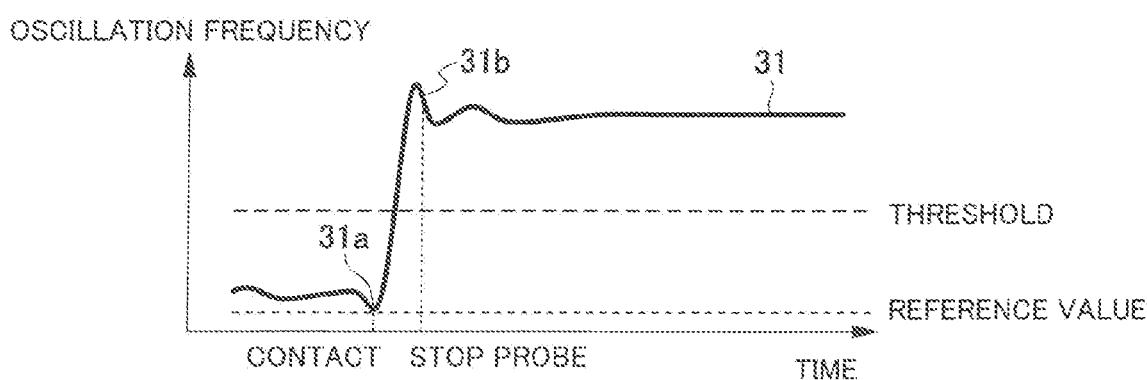
FIG. 4 is a graph showing an example of a capacitance waveform when a liquid level is normally detected according to an embodiment of the invention.

FIG. 4 is a graph showing an example of a capacitance waveform when a liquid level is normally detected. In FIG.

4, a horizontal axis represents time, and a vertical axis represents the oscillation frequency (correlated to the capacitance value). The sample to be inspected is presumed to be in a normal state.

Even after the liquid level detection operation starts and ends (the dispensing probe 1a stops), the CR oscillation circuit 4 outputs an AC signal. The storage unit 6 stores, as time-series data, data of an AC signal from when the dispensing probe 1a starts to be lowered until a certain time elapses after the dispensing probe 1a comes into contact with the liquid level and stops. A change in capacitance at this time appears as a change in the oscillation frequency of the AC signal (capacitance waveform) as shown in FIG. 4.

When the tip portion 1e of the dispensing probe 1a is away from the peripheral portion by a certain distance, an oscillation frequency of a waveform 31 becomes a value near a predetermined reference value or a value greater than the reference value. While the dispensing probe 1a is lowered, the capacitance hardly changes or merely slightly changes, and does not exceed the threshold indicated by a broken line. However, when the tip portion 1e of the dispensing probe 1a comes into contact with the liquid level (timing 31a), the capacitance value exceeds the threshold, and the dispensing probe 1a stops (timing 31b). Immediately after the dispensing probe 1a is stopped, the oscillation frequency fluctuates, which is considered to be due to fluctuation of the liquid level. Thereafter, since there is no change in the state (liquid level contact) of the tip portion 1e of the dispensing probe 1a and the peripheral portion, the capacitance value converges to a substantially constant value.

<Liquid Level Deviation Determination and Liquid Level Deviation Factor Determination>

Figure 5:
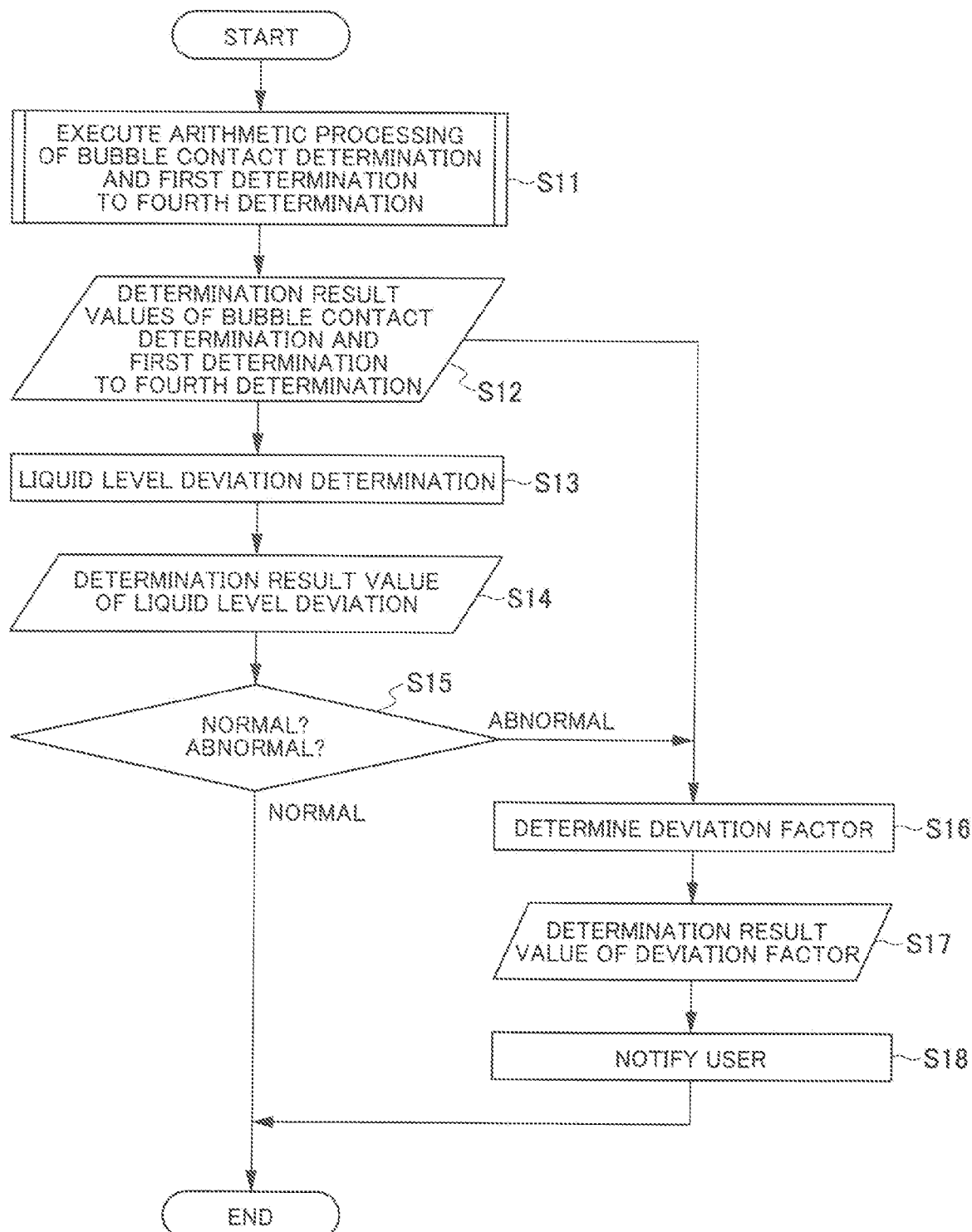
FIG. 5 is a flowchart illustrating an example of a procedure of liquid level deviation determination and deviation factor determination by a second processing unit of the automatic analyzer according to an embodiment of the invention.

FIG. 5 is a flowchart illustrating an example of a procedure of liquid level deviation determination and deviation factor determination by the second processing unit 7 of the automatic analyzer 10. This process is realized by the second processing unit 7 and the second controller 8 of FIG. 1.

In the second processing unit 7, first, each of the bubble contact determination processing unit 72A and the first liquid level deviation determination processing unit 72B to the fourth liquid level deviation determination processing unit 72E (see FIG. 1) executes each arithmetic processing of bubble contact determination and first determination to fourth determination (step S11). The time-series data output from the CR oscillation circuit 4 and stored in the storage unit 6 (FIG. 1) is first divided into a set of short certain sections by the calculation unit 71, and a feature amount (minimum value, maximum value, etc.) is computed and extracted for each of the certain sections. Then, the extracted feature amount is output from the calculation unit 71 as a data series. The data series output from the calculation unit 71 is processed in each of the bubble contact determination processing unit 72A and the first liquid level deviation determination processing unit 72B to the fourth liquid level deviation determination processing unit 72E. Then, each of the bubble contact determination processing unit 72A and the first liquid level deviation determination processing unit 72B to the fourth liquid level deviation determination processing unit 72E outputs a determination result value represented by a binary value of normal (Pass) or abnormal (Fail) to the second controller 8 (step S12).

The second controller 8 uses respective determination result values of the bubble contact determination processing unit 72A and the first liquid level deviation determination processing unit 72B to the fourth liquid level deviation determination processing unit 72E to perform liquid level deviation determination based on a combination thereof (step S13), and outputs a determination result value of liquid level deviation (step S14). This liquid level deviation determination is performed with reference to the liquid level deviation and deviation factor determination table 41 of FIG. 6 to be described later.

Subsequently, the second controller 8 determines whether the liquid level deviation determination result value of step S14 is normal or abnormal (step S15). When it is determined in step S15 that the value is normal (when determination of step S15 corresponds to "normal"), the second processing unit 7 and the second controller 8 end the liquid level deviation determination and deviation factor determination process of FIG. 5.

On the other hand, when the liquid level deviation determination result value is abnormal (when determination of step S15 corresponds to "abnormal"), the second controller 8 uses respective determination result values of the bubble contact determination processing unit 72A and the first liquid level deviation determination processing unit 72B to the fourth liquid level deviation determination processing unit 72E to determine a deviation factor (step S16). Then, the second controller 8 outputs a determination result value of the deviation factor (step S17). This deviation factor determination is performed with reference to the liquid level deviation and deviation factor determination table 41 of FIG. 6 to be described later.

Subsequently, the second controller 8 notifies the user of a determination result of whether the tip portion 1e of the dispensing probe 1a and the liquid level are separated from each other and a status of the deviation factor by displaying the determination result and the status on the screen of the display unit 25 (step S18). At this time, when the liquid level deviation determination corresponds to "Fail", the user is notified of a recommended coping procedure for the factor. When this process ends, the second processing unit 7 and the second controller 8 end the liquid level deviation determination and deviation factor determination process of FIG. 5.

<Liquid Level Deviation and Deviation Factor Determination Table>

FIG. 6 illustrates an example of the liquid level deviation and deviation factor determination table illustrating a combination of respective determination results of the bubble contact determination process and the first determination process to the fourth determination process and the deviation factor.

The liquid level deviation and deviation factor determination table 41 of FIG. 6 has respective items of "bubble contact determination", "first determination", "second determination", "third determination", "fourth determination", "liquid level deviation determination normal or abnormal", and "first candidate for deviation factor". In the liquid level deviation and deviation factor determination table 41 illustrated in FIG. 6, patterns are classified for each combination of these determination processing results, and the classified pattern and the liquid level deviation factor are associated with each other. 32 types of patterns of "pattern 0" to "pattern 31" are registered in the liquid level deviation and deviation factor determination table 41 illustrated in FIG. 6.

Deviation factors are classified into three categories of "contact", "bubble", and "static electricity". The combination table of FIG. 6 is stored in advance in the automatic analyzer 10 (for example, the nonvolatile storage 27), and is referred to during liquid level deviation determination and deviation factor determination. As the deviation factor, a ratio of occurrence of each combination pattern is obtained from a result obtained by an experiment using the automatic analyzer 10, and a highest ratio is determined as the most likely factor. Therefore, a correspondence between the deviation factor and the combination pattern can change depending on the configuration of the automatic analyzer 10 and a threshold of the determination logic. In addition, the deviation factor is resumed to have a high probability and is not a decision. Therefore, while listing other deviation factors, first, the deviation factor is displayed on the screen of the display unit 25 as a factor to be confirmed preferentially and notified to the user.

For example, pattern 0 is a case where all the processing results of the bubble contact determination, the first determination, the second determination, the third determination, and the fourth determination correspond to 'Pass', the liquid level deviation determination result corresponds to 'Normal', and the liquid level deviation factor corresponds to 'not applicable (N/A)'. In addition, Pattern 1 is the case where the processing result of the bubble contact determination corresponds to 'Fail', and the processing result of each of the first determination to the fourth determination corresponds to 'Pass', the liquid level deviation determination result corresponds to 'abnormal', and the liquid level deviation factor corresponds to 'bubble'. In addition, Pattern 3 is the case where the processing result of the bubble contact determination corresponds to 'Fail', the processing result of each of the first determination to the third determination corresponds to 'Pass', the processing result of the fourth determination corresponds to 'Fail'. In pattern 3, the liquid level deviation determination result corresponds to 'abnormal', and the liquid level deviation factor corresponds to 'static electricity'. In association with each of these deviation factors, the recommended coping procedure may be notified to the user.

<Deviation Factor Determination Result and Recommended Coping Procedure>

FIG. 7 illustrates an example of a recommended coping procedure table in which a recommended coping procedure for a deviation factor determination result is registered.

The recommended coping procedure table 42 of FIG. 7 has items of "deviation factor determination result" and "recommended coping procedure displayed on monitor". In the recommended coping procedure table 42, for 'contact' corresponding to the deviation factor, an example sentence 'Check if container is set correctly. If sample volume is small, transfer sample to small-capacity container.' is shown as the recommended coping procedure displayed on the monitor.

In addition, for 'bubble' corresponding to the deviation factor, an example sentence 'Remove bubbles on sample surface.' is shown as the recommended coping procedure.

In addition, for 'static electricity' corresponding to the deviation factor, an example sentence 'Wipe sample container with damp cloth' is shown as the recommended coping procedure.

Further, for 'unclear' corresponding to the deviation factor, an example sentence 'Check for contact, bubble and static electricity.' is shown as the recommended coping procedure. The case where it is determined as unclear is the case of a combination in which five determination results may not exist.

<Details of Operation of Second Processing Unit>

Next, a description will be given of details of each of the bubble contact determination process and the first determination process to the fourth determination process by the second processing unit 7 corresponding to a subroutine of step S11 of FIG. 5.

[Bubble Contact Determination Process]

First, the bubble contact determination process will be described. The bubble contact determination process is executed by the calculation unit 71 and the bubble contact determination processing unit 72A.

FIG. 8 is a flowchart illustrating an example of a procedure of the bubble contact determination process.

Figure 9:
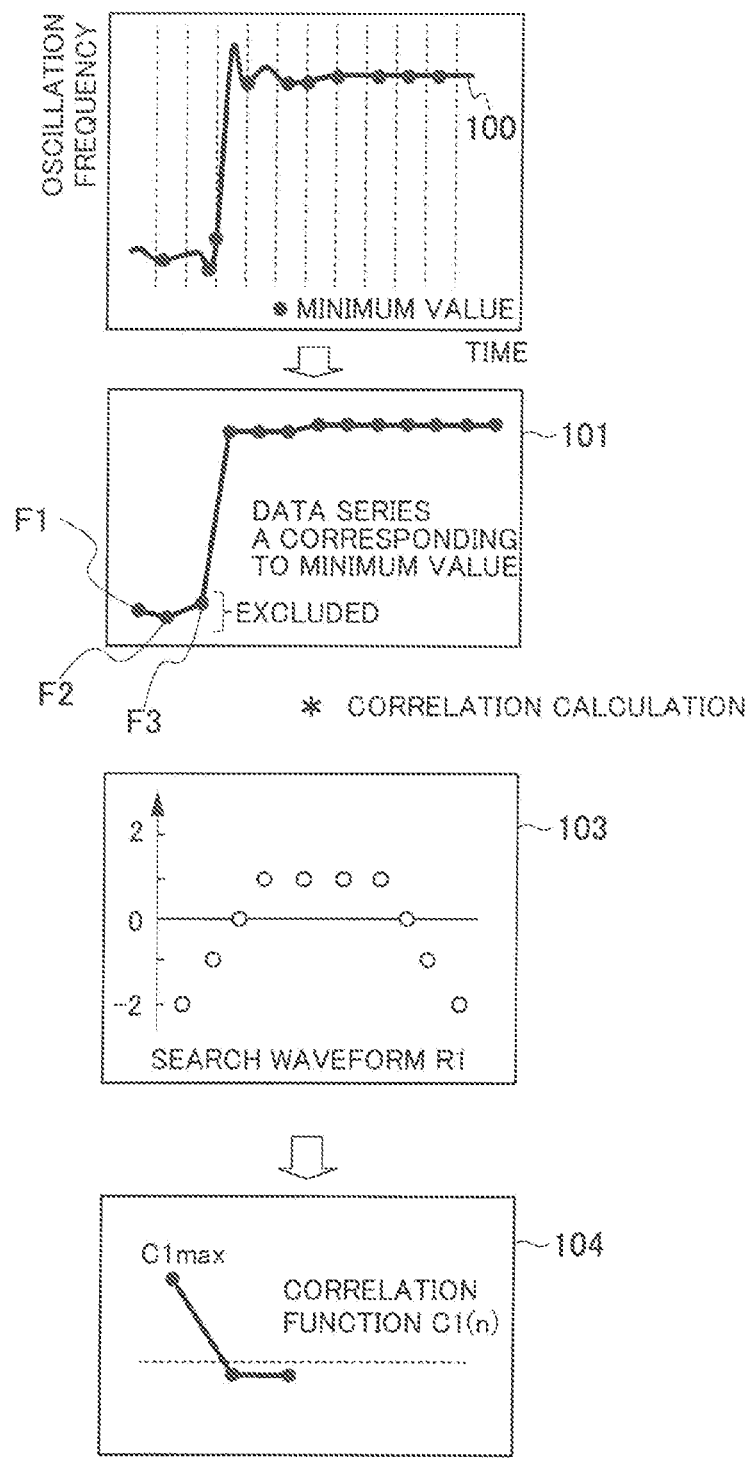
FIG. 9 is a diagram illustrating an image when a capacitance waveform is processed according to an embodiment of the invention.

FIG. 9 is a diagram illustrating an image when a capacitance waveform is processed. In a graph of a waveform 100 of FIG. 9, a horizontal axis represents time as in FIG. 4, and a vertical axis represents an oscillation frequency as in FIG. 4.

First, the calculation unit 71 of the second processing unit 7 acquires time-series data of the oscillation frequency of the AC signal as capacitance waveform data (waveform 100 of FIG. 9) from the data of the AC signal stored in the storage unit 6 (see FIG. 1) (step S21). Subsequently, the calculation unit 71 sets a time region (certain section) at a certain interval from a measurement start (start of lowering of the dispensing probe 1a) to an end for this capacitance waveform data and extracts a minimum value of an oscillation frequency in each time region as a feature amount (step S22). The minimum value as the feature amount is indicated by filled circles in FIG. 9. Then, the calculation unit 71 outputs data of a plurality of minimum values as a data series A (image 101 of FIG. 9) (step S23).

Subsequently, the bubble contact determination processing unit 72A fetches the data series A corresponding to the minimum value from the calculation unit 71, and excludes data before liquid level detection from the data series A corresponding to the minimum value (step S24). The data before liquid level detection refers to a feature amount (minimum value) extracted by the calculation unit 71 before the detector 51 determines that the tip portion 1e of the dispensing probe 1a has come into contact with the liquid level in the container 2. In the image 101 of FIG. 9, the data before the liquid level detection corresponds to feature amounts F1, F2, and F3.

Subsequently, the bubble contact determination processing unit 72A refers to search waveform data R1 (an example of an abnormal waveform model, an image 103 of FIG. 9) registered in advance in the nonvolatile storage 27, etc. (step S25). The search waveform data R1 is an example of a processing filter. In the present embodiment, the search waveform data R1 is set to a waveform having ten points (−2, −1, 0, 1, 1, 1, 1, 0, −1, −2). This search waveform data R1 is designed with the intention of computing a degree of conformity with the abnormal waveform observed when the tip portion 1e of the dispensing probe 1a comes into contact with the bubble on the liquid level in the container 2. The abnormal waveform has a feature that the abnormal waveform rises stepwise and transitions into a mountain shape or a valley shape over a relatively long time such as several milliseconds. The search waveform data R1 includes a negative value due to the intention of setting the same value before and after a correlation process as an average value of feature amounts to which the search waveform data R1 of the data series is applied.

The shape of the search waveform data R1 may correspond to any shape as long as the shape rises stepwise, transitions at the same value for a certain period corresponding to several milliseconds, and then falls stepwise. In addition, the number of functions constituting the search waveform data R1 may correspond to 10 points or more or 10 points or fewer. In addition, another value may be taken as each value of functions constituting the search waveform data R1. It is important that the number of functions constituting the search waveform data R1 (length of the waveform in a time direction) is sufficiently large for a section from when the tip portion 1e of the dispensing probe 1a comes into contact with the liquid level in the container 2 until the dispensing probe 1a stops.

It has been experimentally confirmed that a variation of a waveform of capacitance waveform data acquired when the tip portion 1e of the dispensing probe 1a comes into contact with the bubble generated on the liquid level in the container 2 occurs on the order of 1 to 10 milliseconds. Therefore, when the length of the waveform of the search waveform data R1 in the time direction is set to a length of about several milliseconds, it is possible to monitor the capacitance waveform data in a sufficient section for determining whether the liquid level deviation factor is 'bubble'.

Subsequently, the bubble contact determination processing unit 72A performs correlation calculation using the data series A and the search waveform data R1 (step S26). A correlation function C1(n) used for the correlation calculation is expressed by, for example, Formula (1) below. In Formula (1) below, R1(1) is a set value (function) at a left end of the search waveform data R1, R1(2) is a second set value from the left end, and R1(10) is a set value at a right end. A(n) is an n-th feature amount among the feature amounts constituting the data series A.

$$C1(n)=A(n)*R1(1)+A(n+1)*R1(2)+A(n+2)*R1(3)+A(n+3)*R1(4)+A(n+4)*R1(5)+A(n+5)*R1(6)+A(n+6)*R1(7)+A(n+7)*R1(8)+A(n+8)*R1(9)+A(n+9)*R1(10)$$ Formula (1)

The bubble contact determination processing unit 72A takes '1' to '(number of points of data series A—9)' as a value of n in the above Formula (1), and performs correlation calculation for each n. The point mentioned herein is an extraction point of a feature amount. As a result of the correlation calculation of step S26, a correlation function C1(n) illustrated in an image 104 of FIG. 9 is obtained. Subsequently, the bubble contact determination processing unit 72A obtains a maximum value C1max of the correlation function C1(n) (step S27).

Then, the bubble contact determination processing unit 72A refers to determination thresholds Za and Zb stored in the ROM 22, etc. in advance (step S28), and determines whether a value of the maximum value C1max of the correlation function C1(n) is less than or equal to the determination threshold Za (step S29).

When it is determined in step S29 that the value of the maximum value C1max of the correlation function C1(n) is greater than the value of the determination threshold Za (when step S29 corresponds to NO determination), the bubble contact determination processing unit 72A determines that liquid level detection has not been normally performed (Fail) (step S30). Then, the bubble contact determination processing unit 72A ends the process of this flowchart and proceeds to a process of step S12 of FIG. 5.

On the other hand, when it is determined in step S29 that the value of the maximum value C1max of the correlation function C1(n) is equal to or less than the determination threshold Za (when step S29 corresponds to YES determination), the bubble contact determination processing unit 72A determines whether the value of the maximum value C1max of the correlation function C1(n) is greater than or equal to the determination threshold Zb (step S31). When it is determined in step S31 that the value of the maximum value C1max of the correlation function C1(n) is smaller than the determination threshold Zb (when step S31 corresponds to NO determination), the bubble contact determination processing unit 72A determines that the liquid level detection has not been normally performed (Fail) (step S30).

On the other hand, when it is determined in step S31 that the value of the maximum value C1max of the correlation function C1(n) is smaller than the determination threshold Zb (when step S31 corresponds to NO determination), the bubble contact determination processing unit 72A determines that the liquid level detection has not been normally performed (Fail) (step S30). On the other hand, when it is determined in step S31 that the value of the maximum value C1max of the correlation function is greater than or equal to the determination threshold Zb (when step S31 corresponds to YES determination), the bubble contact determination processing unit 72A determines that the liquid level detection has been normally performed (Pass) (step S32). Then, the bubble contact determination processing unit 72A ends the process of this flowchart and proceeds to a process of step S12 of FIG. 5.

That is, when the value of the maximum value C1max of the correlation function is greater than or equal to the determination threshold Zb and less than or equal to the determination threshold Za, the bubble contact determination processing unit 72A determines that the liquid level detection has been normally performed (Pass). When the value of the maximum value C1max of the correlation function is smaller than the determination threshold Zb or larger than the determination threshold Za, it is determined that the liquid level detection has not been normally performed (Fail).

When it is determined that the liquid level detection has not been normally performed, the bubble contact determination processing unit 72A may notify the user of a determination result via the display unit 9.

Next, data processing for the capacitance waveform data by the calculation unit 71 and the bubble contact determination processing unit 72A will be described with a specific example. Description will be given of both a capacitance waveform when the liquid level detection has been normally performed (hereinafter referred to as a "normal waveform") and a capacitance waveform when the liquid level detection has not been normally performed (hereinafter referred to as an "abnormal waveform").

(Example of Data Processing for Normal Waveform)

Figure 10:
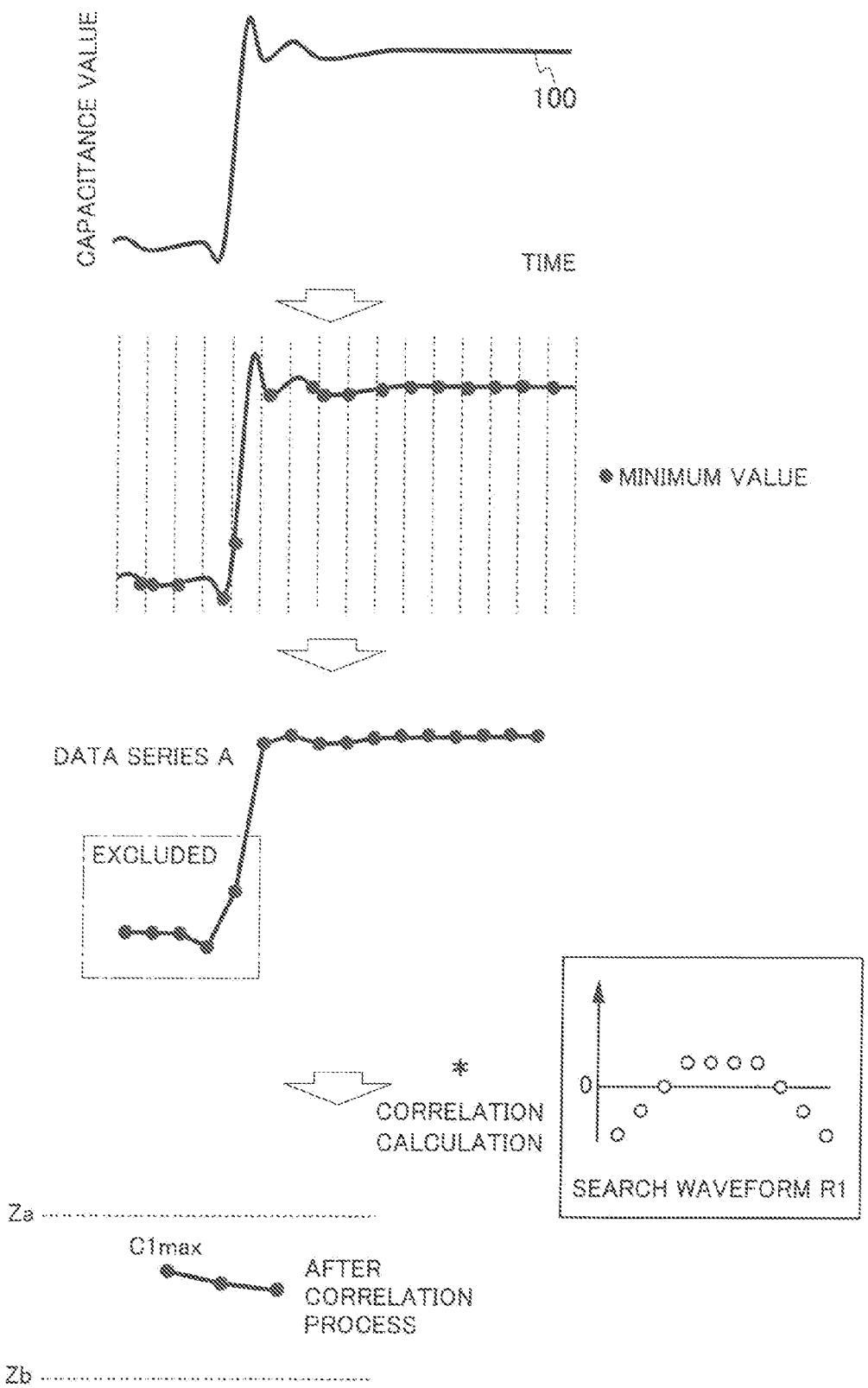
FIG. 10 is a diagram illustrating data processing and a determination process for a normal waveform according to an embodiment of the invention.

FIG. 10 is a diagram illustrating data processing and a determination process for a normal waveform.

A characteristic of the normal waveform is shown as a waveform (normal waveform) 100 at the top of FIG. 10. The characteristic of the normal waveform 100 is that a capacitance value (detected as an oscillation frequency of the CR oscillation circuit 4) transiently rises and then settles down to fluctuate with a small width (the same applies to the waveform 31 of FIG. 4). A first reason why the normal waveform 100 has such a characteristic is that a capacitance value in the air in which the dispensing probe 1a is lowered is greatly different from a capacitance value when the tip portion 1e comes into contact with the liquid level. A second reason is that the capacitance value in each of a state in which the tip portion 1e is in the air and a state after the tip portion 1e comes into contact with the liquid level is stable.

The normal waveform 100 has a flat shape after settling down to fluctuate with a small width, that is, after detecting the liquid level. Therefore, a result of correlation calculation by the bubble contact determination processing unit 72A is a value close to 0. Therefore, the value of the maximum value C1max of the correlation function C1(n) is constant, and the maximum value C1max is within a range defined by the determination thresholds Zb and Za. Therefore, a result of the bubble contact determination by the bubble contact determination processing unit 72A is 'PASS'.

Figure 11:
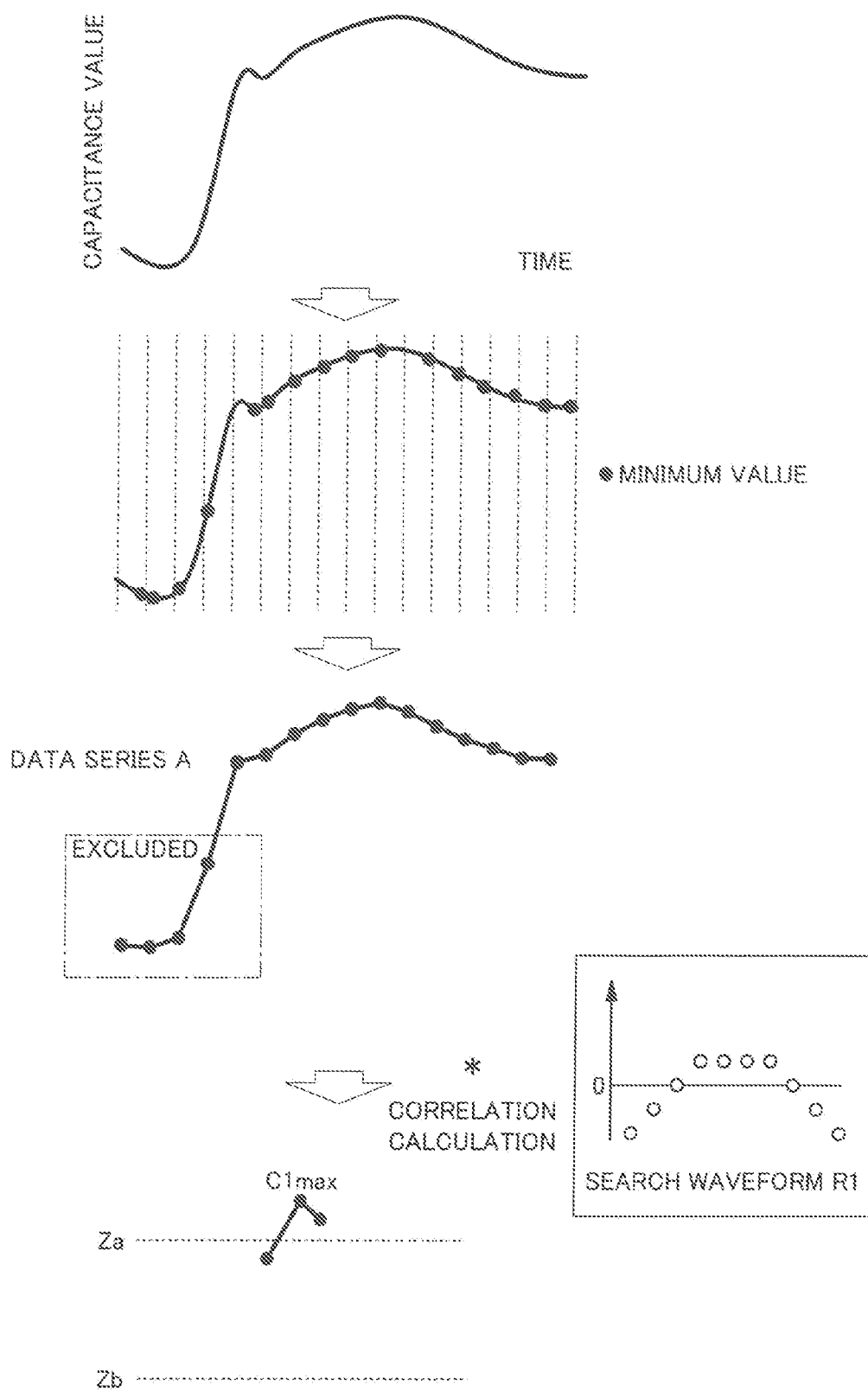
FIG. 11 is a diagram illustrating an example of a capacitance waveform (mountain shape) that can occur when a tip portion of a dispensing probe comes into contact with a bubble and stops, data processing, and a determination process according to an embodiment of the invention.
Figure 12:
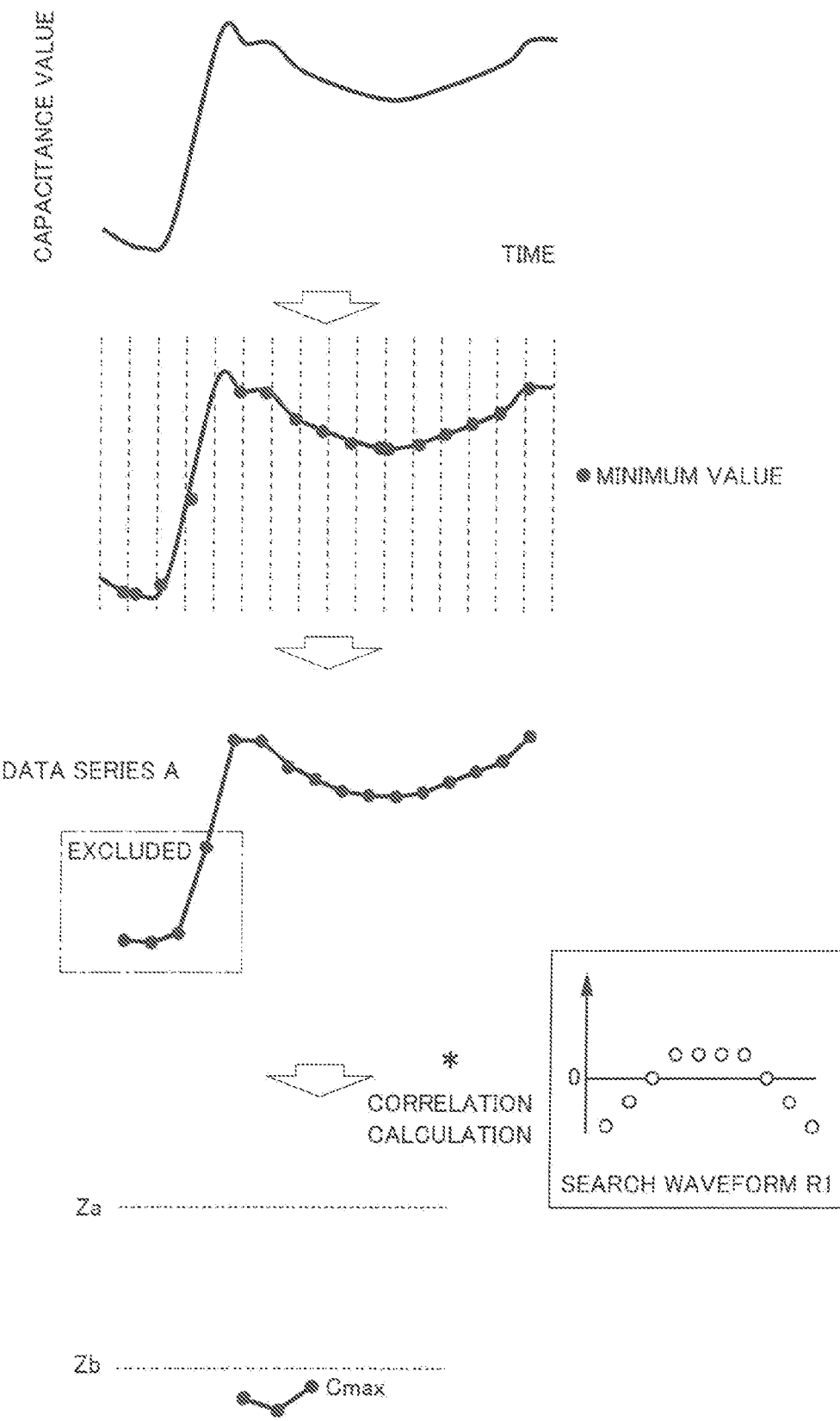
FIG. 12 is a diagram illustrating an example of a capacitance waveform (valley shape) that can occur when the tip portion of the dispensing probe comes into contact with a bubble and stops, data processing, and a determination process according to an embodiment of the invention.

FIG. 11 and FIG. 12 are diagrams illustrating an example of a capacitance waveform that can occur when the tip portion 1e of the dispensing probe 1a comes into contact with a bubble and stops, data processing, and a determination process.

The container 2 contains a liquid (sample 3) such as a biological sample or a clinical test reagent. It is known that bubbling occurs due to a component of the biological sample, and it is known that bubbling occurs when the clinical test reagent contains a surfactant. When the dispensing probe 1a is stopped in a state of coming into contact with the surface of the bubble, the contact area between the bubble and the tip portion 1e of the dispensing probe 1a may change due to vibration at the time of stopping. In addition, the vibration generated when the dispensing probe 1a is stopped is transmitted to the bubble, which may cause vibration in the bubble and change the shape of the bubble.

Since the biological sample or the clinical test reagent generally contains an electrolyte component, the fact that the bubble comes into contact with the tip portion 1e of the dispensing probe 1a means that the dispensing probe 1a and the bubble are electrically connected to each other. Further, the fact that the contact area with the bubble or the shape of the bubble changes means that the area of a sample portion electrically connected to the dispensing probe 1a through the bubble constantly changes. This fact means that the area of the entire conductive substance including the dispensing probe 1a changes with respect to a peripheral portion of the dispensing probe 1a (for example, the ground of the device housing), and the capacitance between two opposing conductors varies with changes in the area of the conductors. Therefore, when the bubble comes into contact with the tip portion 1e of the dispensing probe 1a, the capacitance value randomly increases or decreases.

Figure 13A:
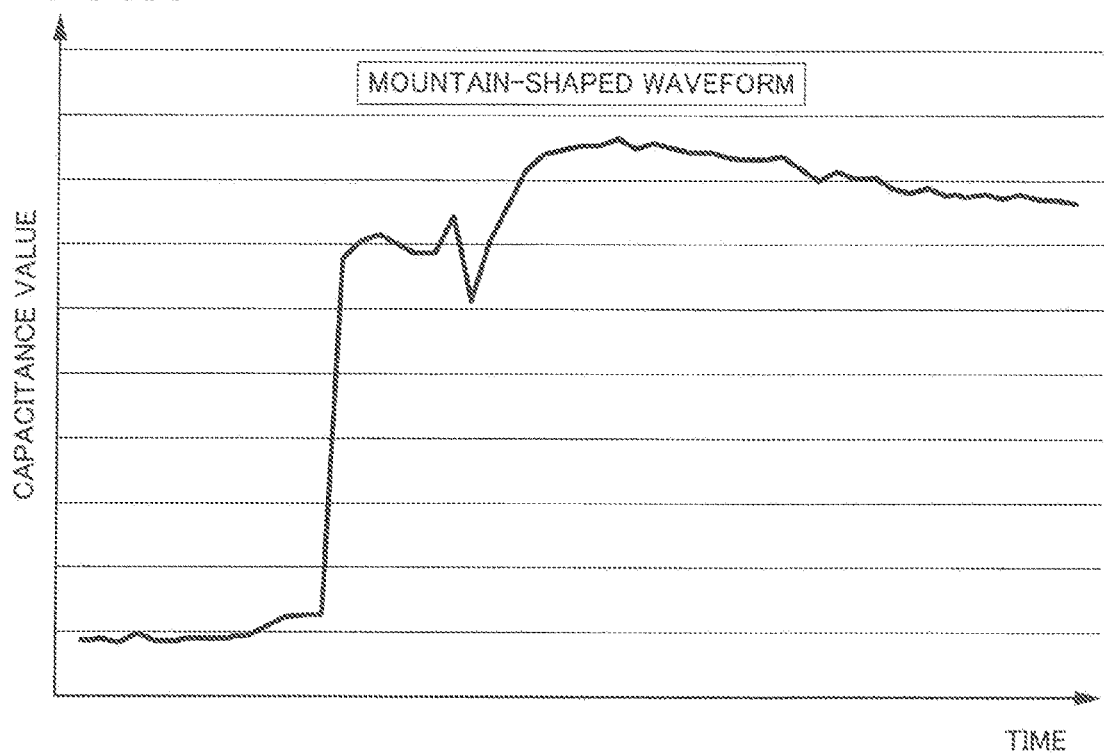
FIGS. 13A and 13B are diagrams illustrating examples of a waveform observed when liquid level detection is actually performed on a bubble according to an embodiment of the invention.
Figure 13B:
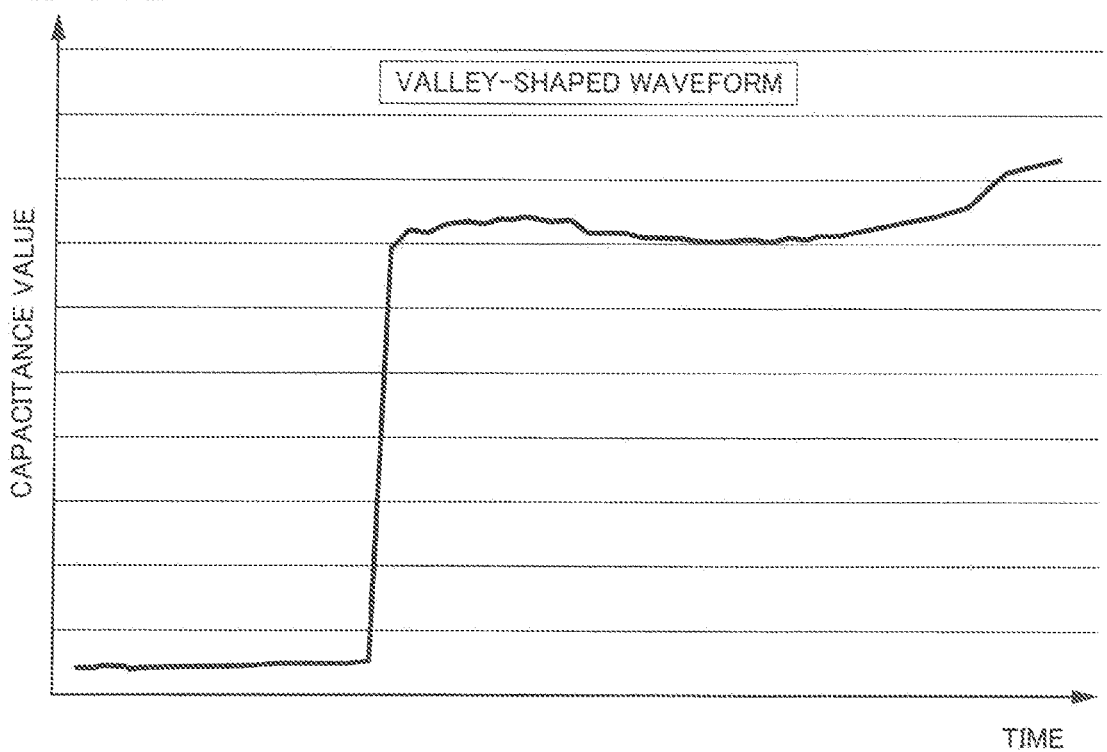

The change in the capacitance value in this case is observed on the order of 1 to 10 milliseconds, which is a gradual variation compared to the variation at the time of abrupt increase in the capacitance due to the liquid level contact. FIG. 11 illustrates an example in which the capacitance value varies in a mountain shape, and FIG. 12 illustrates an example in which the capacitance value varies in a valley shape. FIGS. 13A and 13B illustrate examples of a waveform observed when the liquid level detection is actually performed on the bubble using a liquid level detection mechanism having a configuration close to that of the embodiment of the invention. FIG. 13A is a diagram illustrating an example of a mountain-shaped waveform, and FIG. 13B is a diagram illustrating an example of a valley-shaped waveform.

In variation of the mountain shape illustrated in FIG. 11, the correlation function (search waveform data R1) conforms with the data series A, and thus the value of the maximum value C1max of the correlation function $C1(n)$ is higher than that when the liquid level is normally detected. In this way, the value of the maximum value C1max of the correlation function exceeds the threshold Za, and thus a result of the bubble contact determination corresponds to 'Fail'.

In variation of the valley shape illustrated in FIG. 12, the correlation function (search waveform data R1) does not conform with the data series A. However, since the valley shape is a reverse of the mountain shape, a value calculated by the correlation calculation is a numerical value obtained by inverting the waveform of the mountain shape in a negative direction from a reference value. That is, the value of the maximum value C1max of the correlation function is a significantly lower value than that when the liquid level detection is normally performed. In this way, the value of the maximum value C1max of the correlation function is less than the threshold Zb, and a result of the bubble contact determination corresponds to 'Fail'.

Thus, in the bubble contact determination process, the calculation unit 71 samples the capacitance value at an appropriate time interval from before the liquid level detection to after the detection. Subsequently, the calculation unit 71 extracts a feature amount of sampled data (time-series data) for each certain number of pieces, and creates and outputs the data series A based on the feature amount. Subsequently, the bubble contact determination processing unit 72A computes a correlation with the abnormal waveform model for the data series A, and determines whether the liquid level has been normally detected based on a result of computing the correlation. The abnormal waveform model is a waveform model generated based on a waveform observed when the tip portion 1e of the dispensing probe 1a comes into contact with a bubble on the liquid level in the container 2. By this bubble contact determination process, it is possible to verify whether the shape of the change in the capacitance waveform is close to the abnormal waveform model, and thus it is possible to increase the determination accuracy for erroneous detection when the liquid level deviation factor is a bubble.

In the above-described embodiment, an example in which the minimum value is extracted as the feature amount of the time-series data A has been described. However, the maximum value may be extracted.

[First Determination Process]

Next, the first determination process will be described. The first determination process is executed by the calculation unit 71 and the first liquid level deviation determination processing unit 72B.

Figure 14:
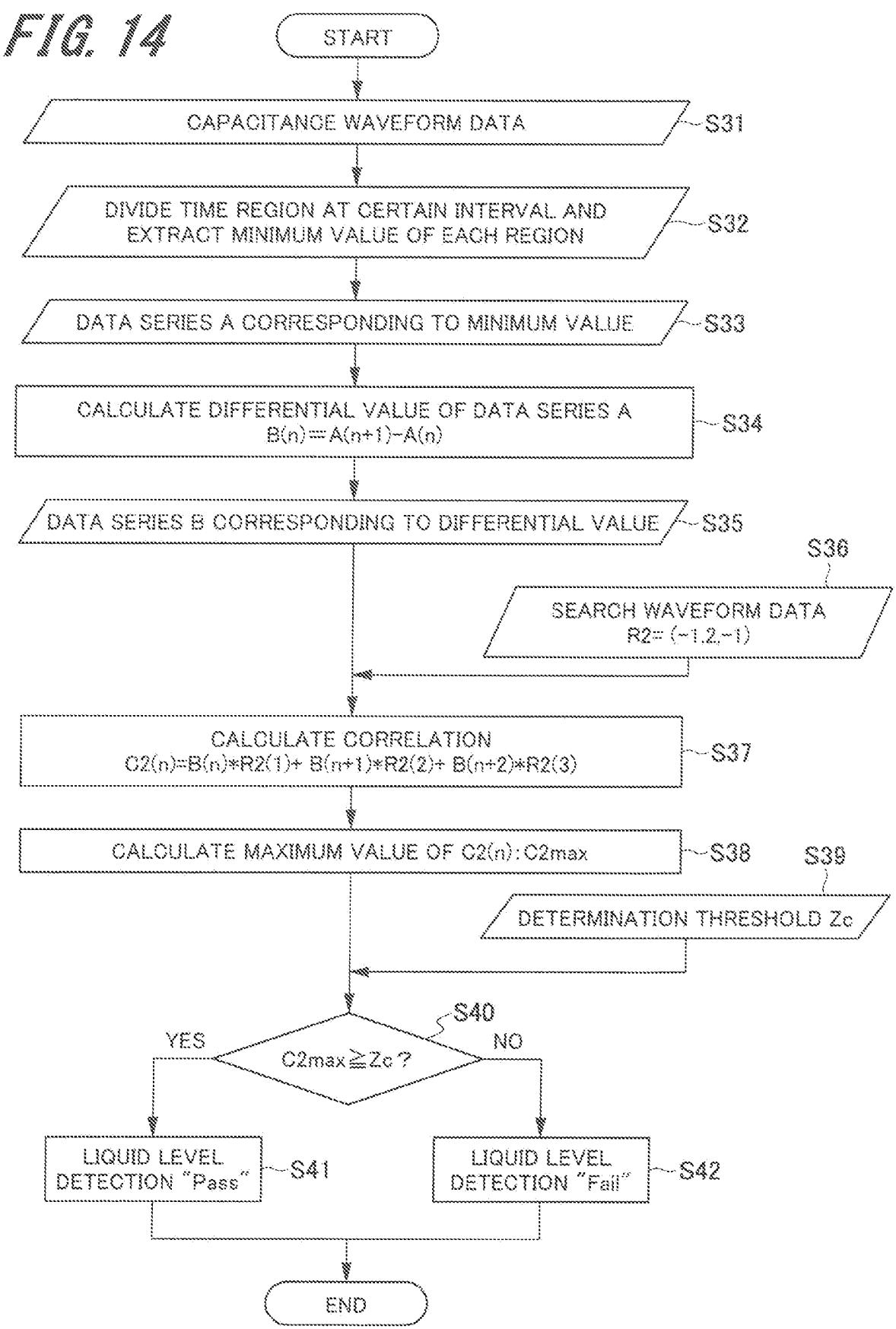
FIG. 14 is a flowchart illustrating an example of a procedure of the first determination process according to an embodiment of the invention.

FIG. 14 is a flowchart illustrating an example of a procedure of the first determination process.

Figure 15:
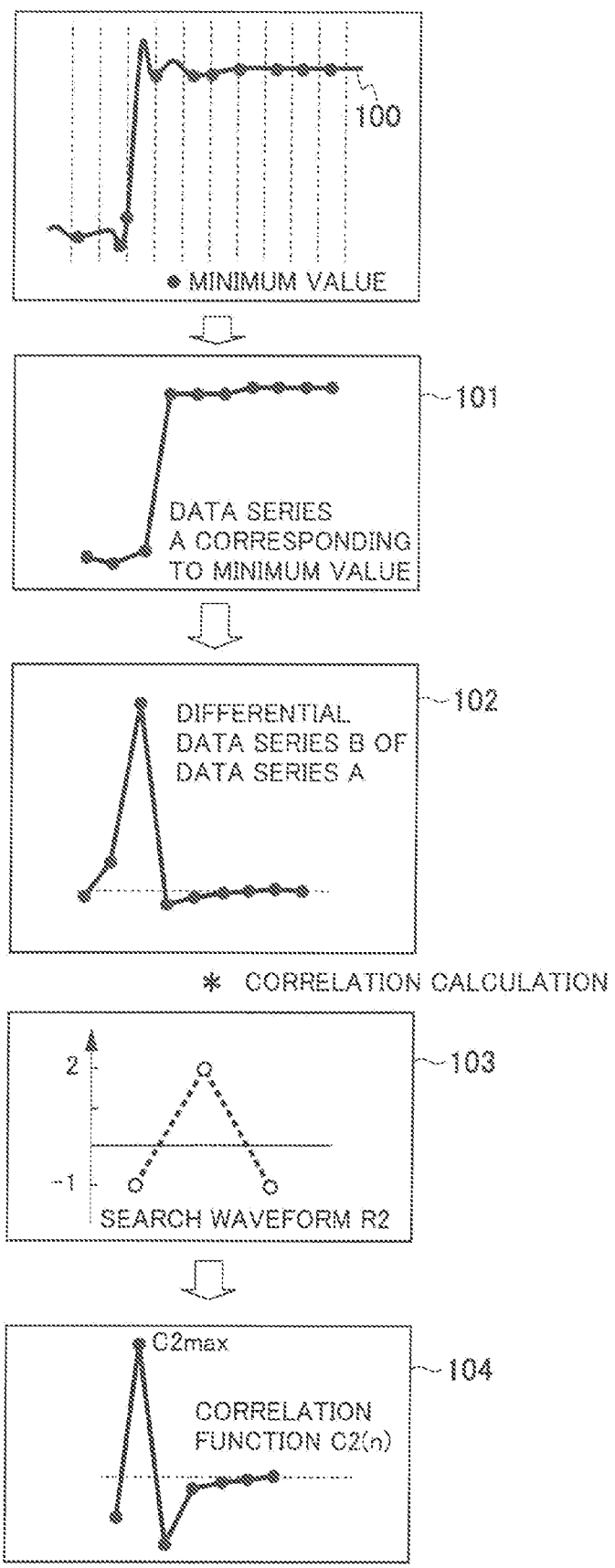
FIG. 15 is a diagram illustrating an image when a capacitance waveform is processed according to an embodiment of the invention.

FIG. 15 is a diagram illustrating an image when a capacitance waveform is processed. In a graph of a waveform 100 of FIG. 15, a horizontal axis represents time and a vertical axis represents an oscillation frequency as in FIG. 4.

First, the calculation unit 71 of the second processing unit 7 performs processing of steps S31 to S33 to create the data series A corresponding to the minimum value. Since the processing of steps S31 to S33 is the same as the processing of steps S21 to S23 of FIG. 8, detailed description thereof is omitted.

Subsequently, the first liquid level deviation determination processing unit 72B fetches the data series A corresponding to the minimum value from the calculation unit 71, and performs a differentiation operation on the data series A (step S34). That is, the first liquid level deviation determination processing unit 72B applies a function B(n) of Formula (2) below to each point of the data series A to obtain a data series B (image 102 of FIG. 15) having differential values of the data series A (step S35). In the following Formula (2), 'n' is a natural number.

$$B(n)=A(n+1)-A(n) \qquad \text{Formula (2)}$$

Subsequently, the first liquid level deviation determination processing unit 72B refers to search waveform data R2 (an image 103 of FIG. 15) registered in advance in the nonvolatile storage 27, etc. (step S36). The search waveform data R2 is an example of a processing filter. In the present embodiment, the search waveform data R2 is set to a waveform having three points (−1, 2, −1). This search waveform data R2 is designed with the intention of computing a degree of conformity with a waveform whose value transiently rises, that is, a spike-shaped waveform. The search waveform data R2 includes a negative value due to the intention of setting the same value before and after a correlation process as an average value of feature amounts to which the search waveform data R2 of the data series is applied.

The search waveform data R2 may have any shape as long as the data has a spike-shaped waveform, that is, a shape in which a difference between a certain point and points on both sides thereof is relatively sufficiently large. In addition, the number of functions constituting the search waveform data R2 may correspond to 3 points or more or 3 points or fewer. In addition, another value may be taken as each value of functions constituting the search waveform data R2.

A correlation function C2(n) between the data series B and the search waveform data R2 is expressed by, for example, Formula (3) below. In Formula (3) below, R2(1) is a set value on a left side of three points of the search waveform data R, R2(2) is a set value at a center of the three points, and R2(3) is a set value on a right side of the three points.

$$C2(n)=B(n)*R2(1)+B(n+1)*R2(2)+B(n+2)*R2(3) \quad \text{Formula (3)}$$

The first liquid level deviation determination processing unit 72B takes '1' to '(number of points of data series B−2)' as a value of n, and performs correlation calculation for each n (step S37). As a result of the correlation calculation of step S37, a correlation function C2(n) illustrated in an image 104 of FIG. 15 is obtained. Subsequently, the first liquid level deviation determination processing unit 72B obtains a maximum value C2max of the correlation function C2(n) (step S38).

Then, the first liquid level deviation determination processing unit 72B refers to a determination threshold Zc stored in the ROM 22, etc. in advance (step S39), and determines whether the maximum value C2max of the correlation function is greater than or equal to the determination threshold Zc (step S40).

When the value of the maximum value C2max of the correlation function is greater than or equal to the value of the determination threshold Zc (when step S40 corresponds to YES determination) in step S40, the first liquid level deviation determination processing unit 72B determines that the liquid level detection has been normally performed (Pass) (step S41). Then, the process of this flowchart is ended and the operation proceeds to step S12 of FIG. 5.

On the other hand, when it is determined in step S40 that the value of the maximum value C2max of the correlation function is smaller than the determination threshold Zc (when step S40 corresponds to NO determination), the first liquid level deviation determination processing unit 72B determines that the liquid level detection has not been normally performed (Fail) (step S42). Then, the process of this flowchart is ended and the operation proceeds to step S12 of FIG. 5.

Here, when it is determined that the liquid level detection has not been normally performed, the first liquid level deviation determination processing unit 72B may notify the user of a determination result via the display unit 9.

Thus, in the first determination process, the capacitance value is sampled at an appropriate time interval from before the liquid level detection to after the detection. Subsequently, a feature amount of sampled data (time-series data) is extracted for each certain number of pieces, and a new data series is created and stored based on the feature amount. Then, a correlation with a normal waveform model (for example, a spike-shaped waveform) is obtained for the new data series, and it is determined from a result whether the liquid level could be correctly detected. By this first determination process, it can be determined whether a shape of a change in the capacitance waveform is close to that of a normal waveform.

An example in which the minimum value is extracted as the feature amount of the time-series data has been described. However, the maximum value may be extracted. In addition, the data series is created by a differentiation operation on the feature amount of the time-series data.

[Second Determination Process]

Next, the second determination process will be described. The second determination process is executed by the calculation unit 71 and the second liquid level deviation determination processing unit 72C.

Figure 16:
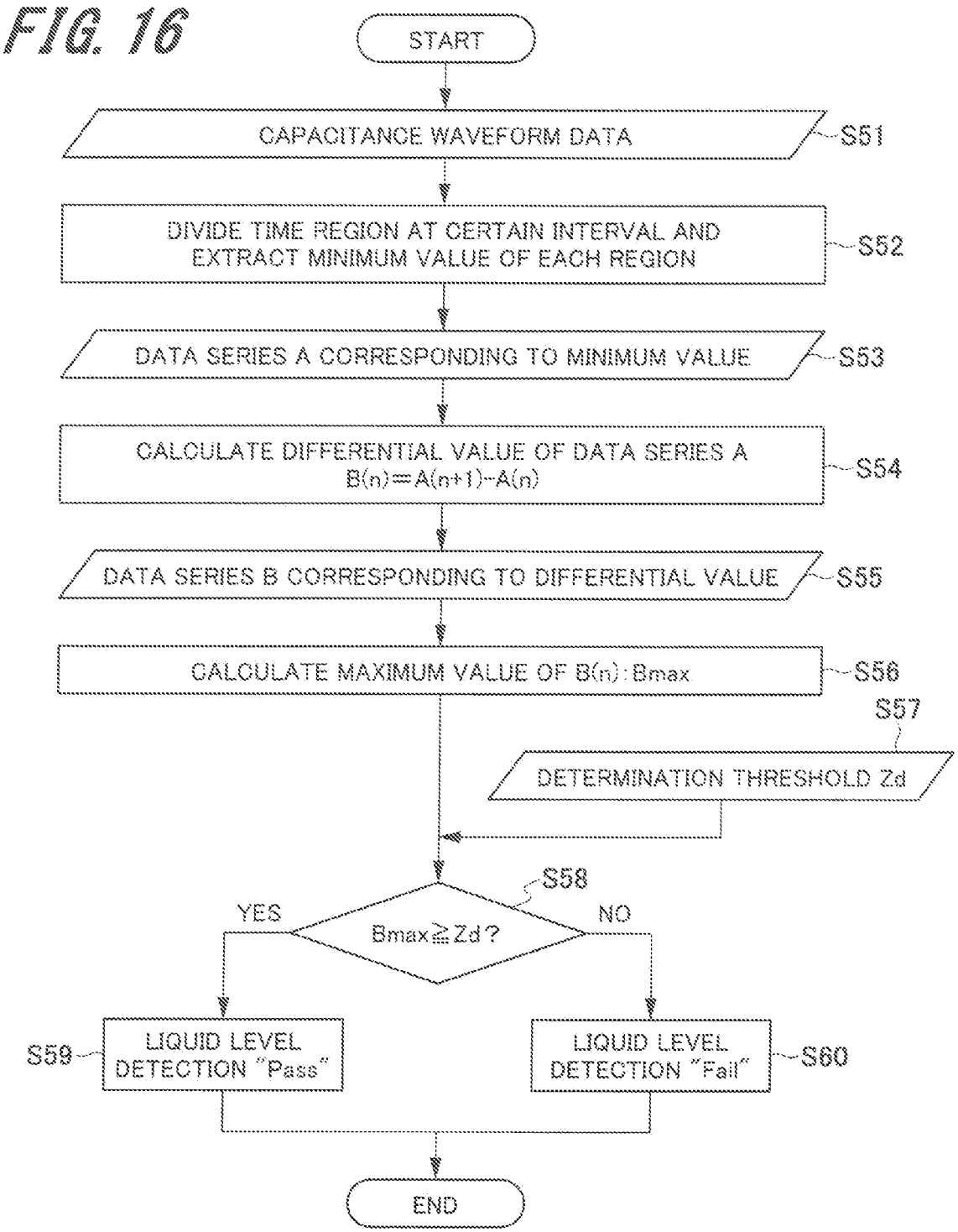
FIG. 16 is a flowchart illustrating an example of a procedure of the second determination process according to an embodiment of the invention.

FIG. 16 is a flowchart illustrating an example of a procedure of the second determination process.

Figure 17:
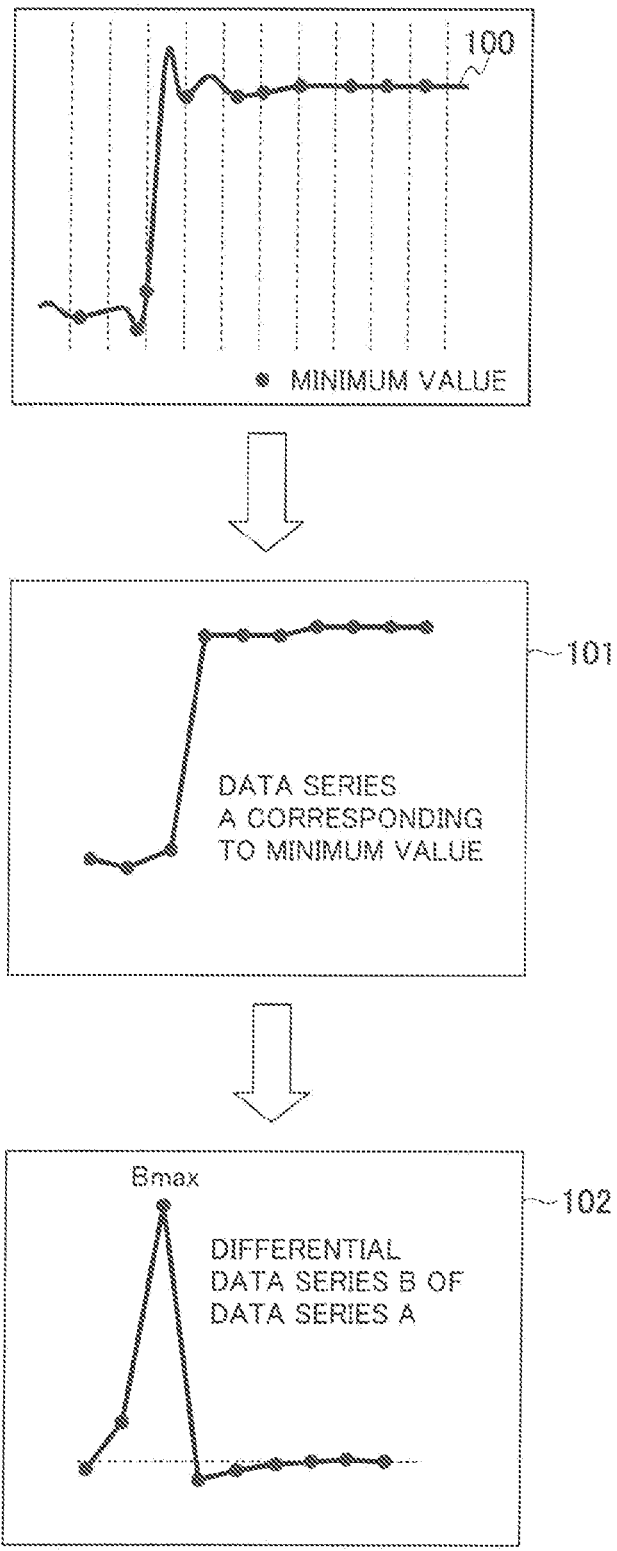
FIG. 17 is a diagram illustrating an image when a capacitance waveform is processed according to an embodiment of the invention.

FIG. 17 is a diagram illustrating an image when a capacitance waveform is processed.

First, the calculation unit 71 of the second processing unit 7 performs processing of steps S51 to S53 to create the data series A corresponding to the minimum value. Since the processing of steps S51 to S53 is the same as the processing of steps S21 to S23 of FIG. 8, detailed description thereof is omitted.

Subsequently, the second liquid level deviation determination processing unit 72C performs processing of steps S54 to S55 to create the data series B corresponding to the differential value. Since the processing of steps S54 to S55 is similar to the processing of steps S34 to S35 of FIG. 14, detailed description thereof is omitted.

Subsequently, the second liquid level deviation determination processing unit 72C obtains a maximum value Bmax (image 102 of FIG. 17) of the function B(n) of the differential value (step S56). The maximum value Bmax corresponds to a size of a largest slope of a waveform based on the data series B of the differential value. Then, the second liquid level deviation determination processing unit 72C refers to a determination threshold Zd stored in the ROM 22, etc. in advance (step S57), and determines whether a value of the maximum value Bmax of the differential value is greater than or equal to the determination threshold Zd (step S58).

When it is determined that the value of the maximum value Bmax of the differential value is greater than or equal to the value of the determination threshold Zd (when step S58 corresponds to YES determination) in step S58, the second liquid level deviation determination processing unit 72C determines that the liquid level detection has been normally performed (Pass) (step S59). Then, the process of this flowchart is ended and the operation proceeds to step S12 of FIG. 5.

On the other hand, when it is determined in step S58 that the value of the maximum value Bmax of the differential value is smaller than the value of the determination threshold Zd (when step S58 corresponds to NO determination), the second liquid level deviation determination processing unit 72C determines that the liquid level detection has not been normally performed (Fail) (step S60). Then, the process of this flowchart is ended and the operation proceeds to step S12 of FIG. 5.

Here, when it is determined that the liquid level detection has not been normally performed, the second liquid level deviation determination processing unit 72C may notify the user of a determination result via the display unit 9.

Thus, in the second determination process, the capacitance value is sampled at an appropriate time interval from before the liquid level detection to after the detection. Subsequently, a feature amount of sampled data (time-series data) is extracted for each certain number of pieces, and a new data series is created and stored based on the feature amount. Then, a maximum value of the new data series is obtained, and it is determined from a result thereof whether the liquid level has been correctly detected. By this second determination process, it can be determined whether the magnitude (steepness) of the change in the capacitance waveform is normal. Even though the second determination process is considered to be effective mainly for contact determination, a final deviation factor is determined based on a combination of five determination results.

An example in which the minimum value is extracted as the feature amount of the time-series data has been described. However, the maximum value may be extracted. In addition, the data series is created by a differentiation operation on the feature amount of the time-series data.

[Third Determination Process]

Next, the third determination process will be described. The third determination process is executed by the calculation unit 71 and the third liquid level deviation determination processing unit 72D.

Figure 18:
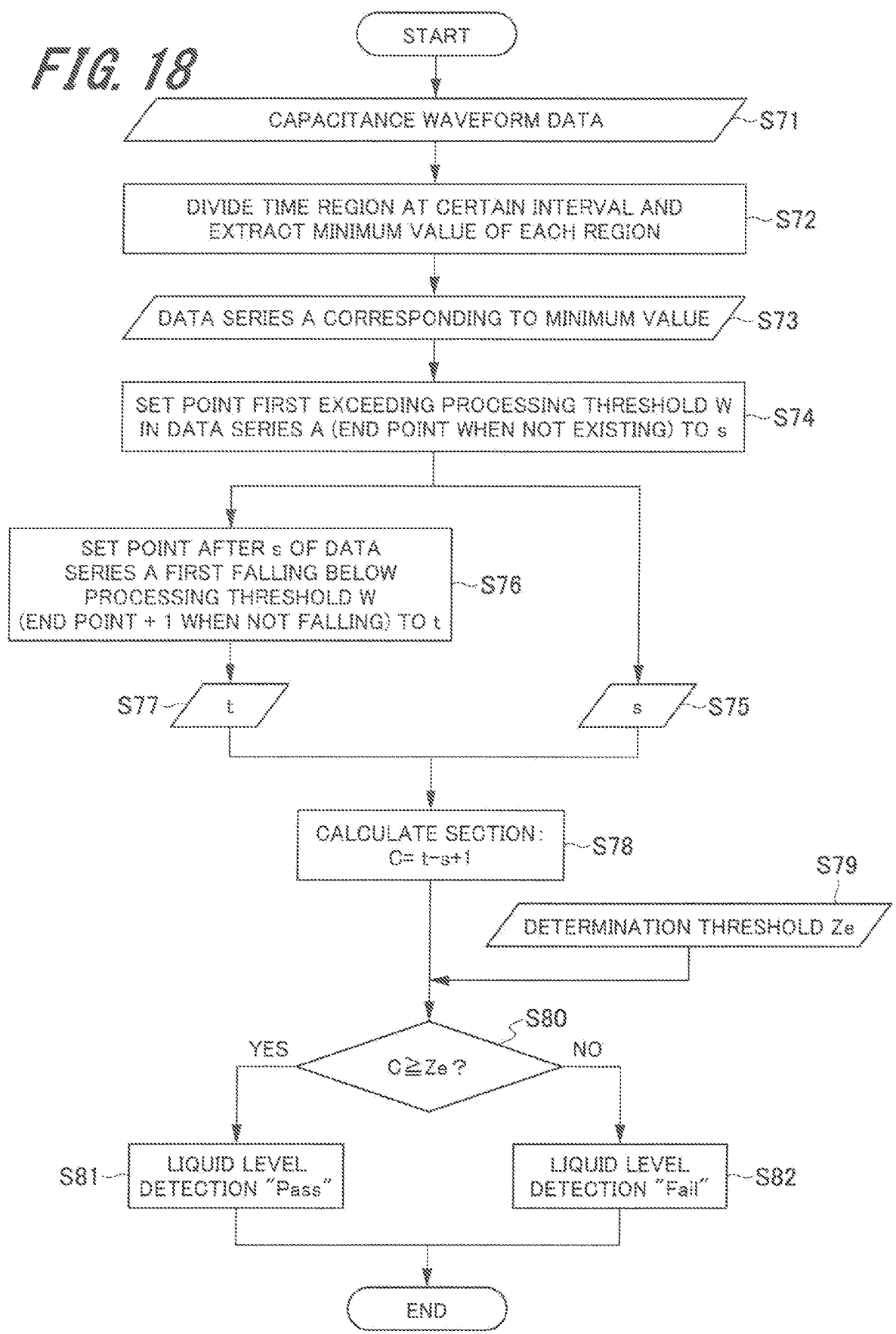
FIG. 18 is a flowchart illustrating an example of a procedure of the third determination process according to an embodiment of the invention.

FIG. 18 is a flowchart illustrating an example of a procedure of the third determination process.

Figure 19:
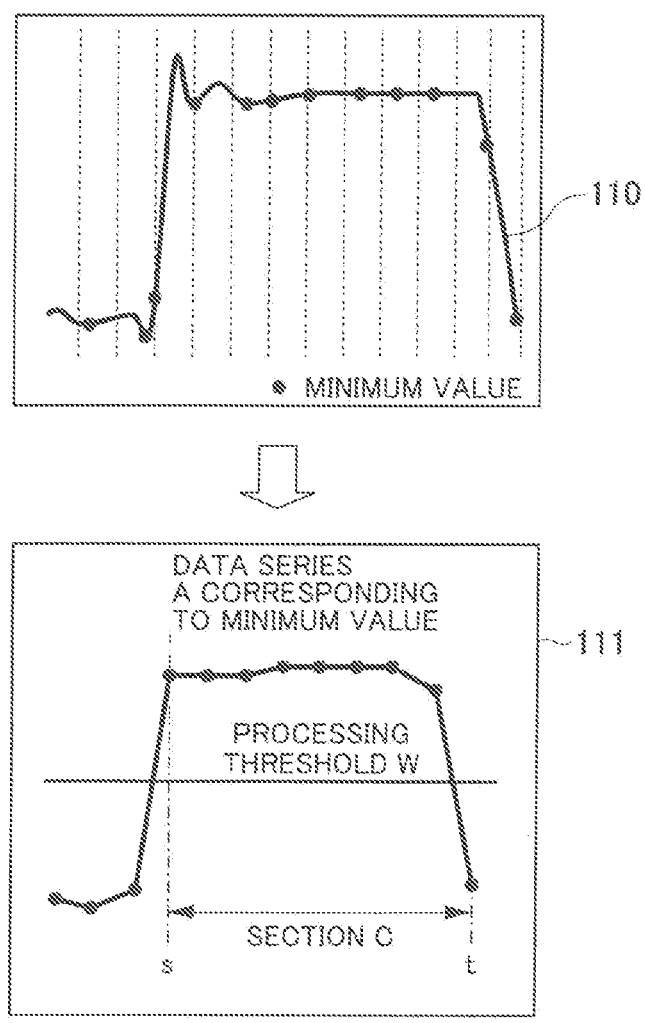
FIG. 19 is a diagram illustrating an image when a capacitance waveform is processed according to an embodiment of the invention.

FIG. 19 is a diagram illustrating an image when a capacitance waveform is processed.

First, the calculation unit 71 of the second processing unit 7 performs processing of steps S71 to S73 on capacitance waveform data (waveform 110 of FIG. 19) to create the data series A corresponding to the minimum value. Since the processing of steps S71 to S73 is the same as the processing of steps S21 to S23 of FIG. 8, detailed description thereof is omitted.

Subsequently, the third liquid level deviation determination processing unit 72D refers to a threshold W for data processing stored in advance in the storage unit 6, and searches for an s-th point that first exceeds the threshold W by counting from a first point of the data series A (steps S74 and S75). In other words, a point that first exceeds the threshold W in the data series A is set as s. Here, the point is an extraction point of a feature amount. When s is not found in the first search, that is, when the point of the data series A does not exceed the threshold W, s is set as an end point (final point) of the data series A.

Subsequently, the third liquid level deviation determination processing unit 72D searches for a point that first falls below the threshold W among points after s in the data series A, and sets the point as t (steps S76 and S77). When there is no point that falls below the threshold W, in other words, when the point of the data series A does not fall below the threshold W after exceeding the threshold W, a value obtained by adding 1 to the end point is set as t.

Subsequently, the third liquid level deviation determination processing unit 72D calculates a length of a section C in which the threshold W of the data series A is exceeded according to Formula (4) (step S78). The length of the section C is indicated as the number of points exceeding the threshold W of the data series A (image 111 of FIG. 19).

$$C = t - s + 1 \quad \text{Formula (4)}$$

Then, the third liquid level deviation determination processing unit 72D refers to a determination threshold Ze stored in the ROM 22, etc. in advance (step S79), and determines whether the length of the section C is greater than or equal to the determination threshold Ze (step S80). This determination threshold Ze is set based on a time from when the tip portion 1e of the dispensing probe 1a comes into contact with the liquid level until the dispensing probe 1a rises.

When it is determined that the length of the section C is greater than or equal to a value of the determination threshold Zc in step S80 (when step S80 corresponds to YES determination), the third liquid level deviation determination processing unit 72D determines that the liquid level detection has been normally performed (Pass) (step S81). Then, the process of this flowchart is ended and the operation proceeds to step S12 of FIG. 5.

On the other hand, when it is determined that the length of the section C is smaller than the value of the determination threshold Zc in step S80 (when step S80 corresponds to NO determination), the third liquid level deviation determination processing unit 72D determines that the liquid level detection has not been normally performed (Fail) (step S82). Then, the process of this flowchart is ended and the operation proceeds to step S12 of FIG. 5.

Here, when it is determined that the liquid level detection has not been normally performed, the third liquid level deviation determination processing unit 72D may notify the user of a determination result via the display unit 9.

Thus, in the third determination process, the capacitance value is sampled at an appropriate time interval from before the liquid level detection to after the detection. Subsequently, for the sampled data (time-series data), a point first exceeding (reaching) a unique threshold W stored in advance and a point that subsequently falls below the threshold W are extracted, and the number of points between the two points is obtained as the length of the section C exceeding the threshold W. Then, it is determined from a result thereof whether the liquid level has been correctly detected. By this third determination process, it can be determined whether the shape of the capacitance waveform is normal (the minimum value continues for a certain number of points or more). Even though the third determination process is considered to be effective mainly for bubble determination, a final deviation factor is determined based on a combination of five determination results.

An example in which the minimum value is extracted as the feature amount of the time-series data has been described. However, the maximum value may be extracted.

[Fourth Determination Process]

Next, the fourth determination process will be described. The fourth determination process is executed by the calculation unit 71 and the fourth liquid level deviation determination processing unit 72E.

Figure 20:
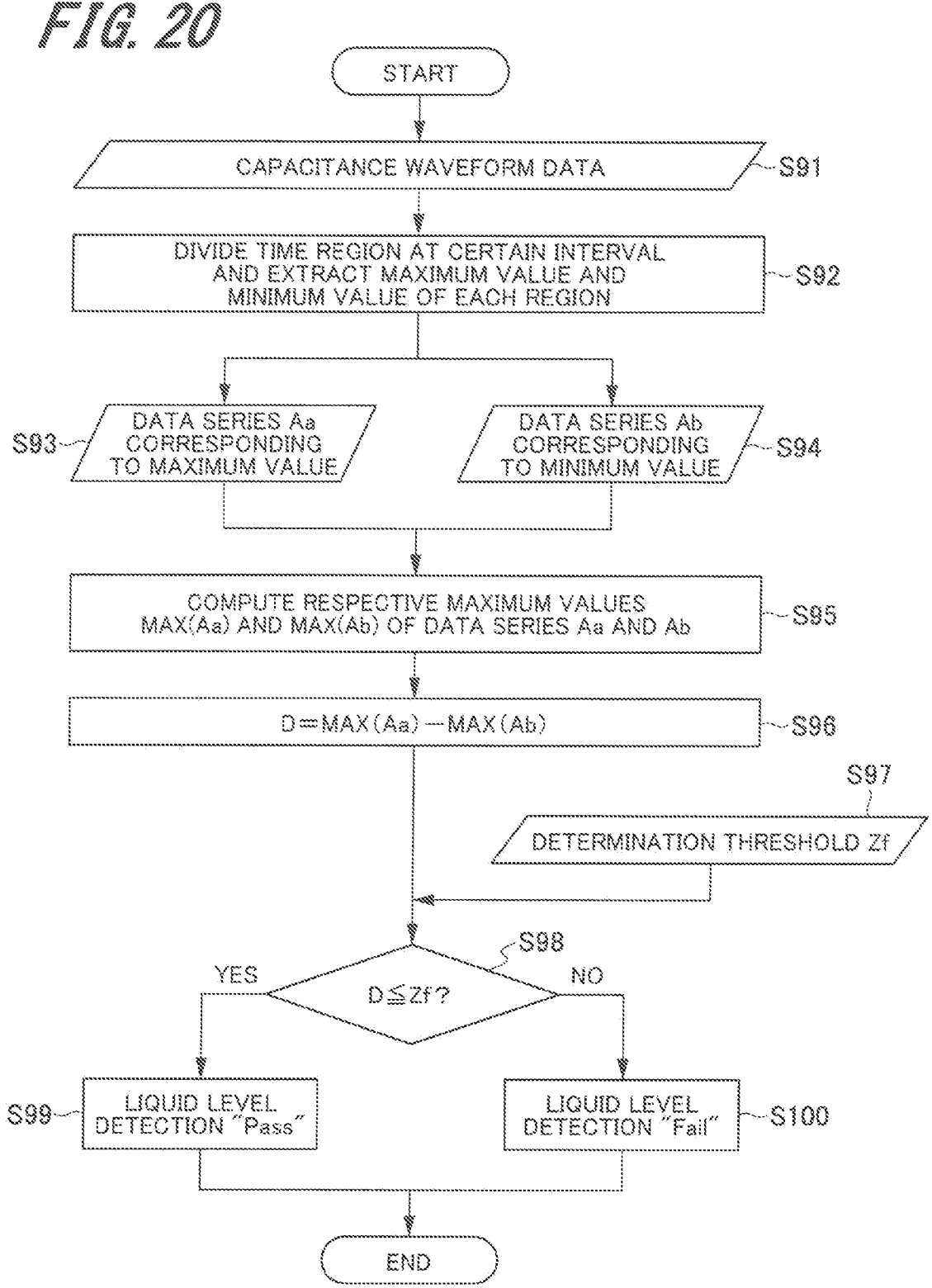
FIG. 20 is a flowchart illustrating an example of a procedure of the fourth determination process according to an embodiment of the invention.

FIG. 20 is a flowchart illustrating an example of a procedure of the fourth determination process.

Figure 21:
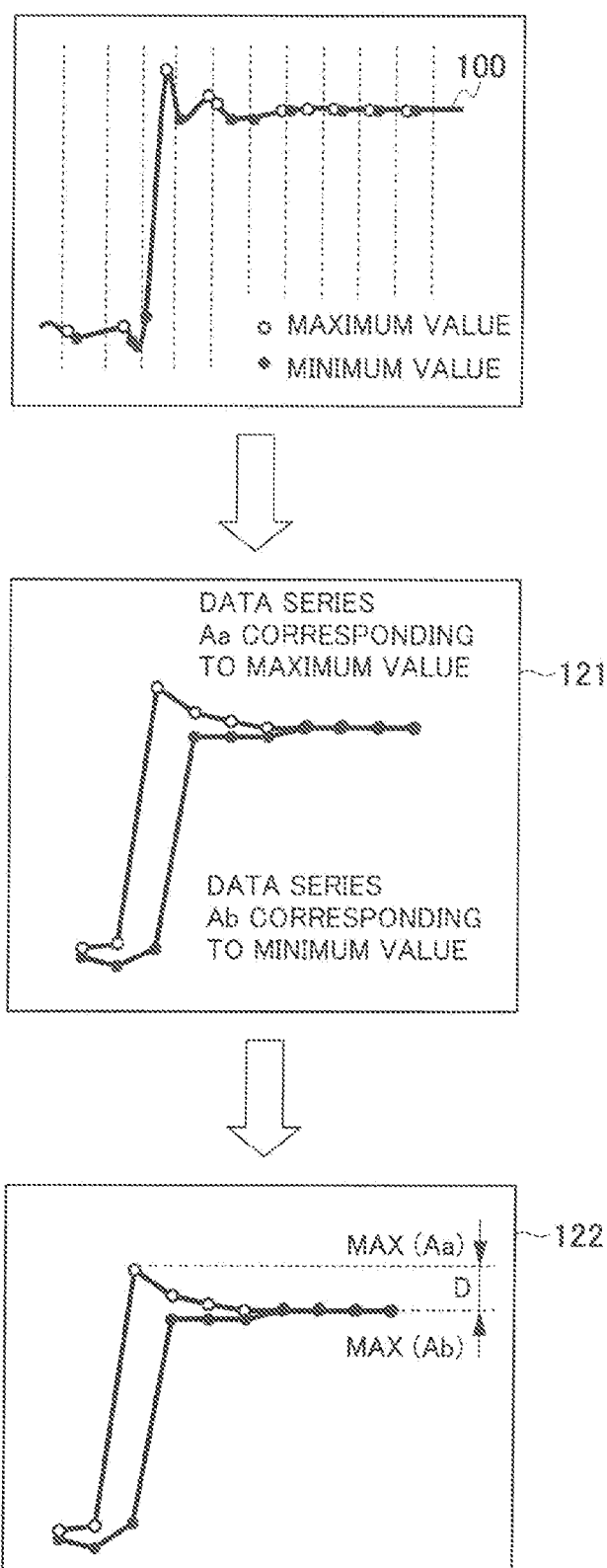
FIG. 21 is a diagram illustrating an image when a capacitance waveform is processed according to an embodiment of the invention.

FIG. 21 is a diagram illustrating an image when a capacitance waveform is processed.

First, the calculation unit 71 of the second processing unit 7 acquires time-series data of the oscillation frequency of the AC signal as capacitance waveform data (waveform 100 of FIG. 21) from the data of the AC signal stored in the storage unit 6 (step S91). Subsequently, the calculation unit 71 sets a time region (certain section) at a certain interval from a measurement start (start of lowering of the dispensing probe 1a) to an end and for this capacitance waveform data and extracts a maximum value (indicated by open circles in FIG. 21) and a minimum value (indicated by filled circles in FIG. 21) of an oscillation frequency in each time region as a feature amount (step S92). Then, the calculation unit 71 outputs data of the maximum value and the minimum value as a data series Aa and a data series Ab (image 121 of FIG. 21) (steps S93 and S94).

Subsequently, the fourth liquid level deviation determination processing unit 72E calculates a maximum value MAX(Aa) of the data series Aa of the maximum value and a maximum value MAX(Ab) of the data series Ab of the minimum value (step S95). Subsequently, the fourth liquid level deviation determination processing unit 72E obtains a numerical value D (difference) obtained by subtracting the maximum value MAX(Ab) from the maximum value MAX (Aa) (image 122 of FIG. 21) (step S96).

In principle, the maximum value MAX(Aa) of the data series Aa of the maximum value is greater than or equal to the maximum value MAX(Ab) of data series Ab of the minimum value at all times, and thus the difference D is a value of '0' or more.

Then, the fourth liquid level deviation determination processing unit 72E refers to a determination threshold Zf stored in the ROM 22, etc. in advance (step S97), and determines whether the difference D is less than or equal to the determination threshold Zf (step S98).

When it is determined that the difference D is less than or equal to a value of the determination threshold Zf in step S98 (when step S98 corresponds to YES determination), the fourth liquid level deviation determination processing unit 72E determines that the liquid level detection has been normally performed (Pass) (step S99). Then, the process of this flowchart is ended and the operation proceeds to step S12 of FIG. 5.

On the other hand, when it is determined that difference D is larger than the value of the determination threshold Zf in step S98 (when step S98 corresponds to NO determination), the fourth liquid level deviation determination processing unit 72E determines that the liquid level detection has not been normally performed (Fail) (step S100). Then, the process of this flowchart is ended and the operation proceeds to step S12 of FIG. 5.

Here, when it is determined that the liquid level detection has not been normally performed, the fourth liquid level deviation determination processing unit 72E may notify the user of a determination result via the display unit 9.

Thus, in the fourth determination process, the capacitance value is sampled at an appropriate time interval from before the liquid level detection to after the detection. Subsequently, a maximum value and a minimum value are extracted as a feature amount of sampled data (time-series data) for each certain number of pieces, and a data series including the maximum value and a data series including the minimum value are created and stored. Then, maximum values of the two data series are obtained, a difference therebetween is calculated, and it is determined from a result thereof whether the liquid level has been correctly detected. By this fourth determination process, it can be determined whether the capacitance waveform has high stability (presence or absence of noise). Even though the fourth determination process is considered to be effective mainly for static electricity determination, a final deviation factor is determined based on a combination of five determination results.

<Various Effects>

In the embodiment described above, the calculation unit 71 divides time-series data of the oscillation frequency of the AC signal output by the oscillation circuit until a certain time elapses after the dispensing probe 1a starts to be lowered for each certain section, extracts the feature amount for each certain section, and outputs the extracted feature amount as the data series A. In addition, the bubble contact determination processing unit 72A computes the correlation between the waveform of the data series A of the feature amount output from the calculation unit 71 and the abnormal waveform model (search waveform data R1) based on the waveform observed when the tip portion 1e of the dispensing probe 1a comes into contact with the bubble on the liquid level in the container 2, and determines whether the liquid level detection has been normally performed based on a result of computing the correlation. Further, the second controller 8 performs liquid level deviation determination based on a determination result value of the bubble contact determination processing unit 72A, and outputs the liquid level deviation determination result value. Therefore, according to the present embodiment, it is possible to improve the determination accuracy of erroneous detection when the liquid level deviation factor is the bubble.

In addition, according to the present embodiment, it is possible to determine that the detection result corresponds to erroneous detection based on a combination of determination results of five determination processes for erroneous detection of liquid level detection of the capacitance method. That is, when the detector 51 detects the liquid level despite the fact that the tip portion 1e of the dispensing probe 1a is not in contact with the liquid level (liquid level deviation), it is possible to determine with higher accuracy that the detection result is erroneous.

In addition, according to the present embodiment, it is possible to estimate a factor corresponding to one of "bubble", "static electricity", "contact", or "unclear" causing liquid level deviation for erroneous detection of the liquid level using a combination of determination results of five determination processes with high probability.

In addition, in the present embodiment, by notifying the user through the display unit 9 that erroneous detection (liquid level deviation) of liquid level detection has occurred, it is possible to prevent the user from reporting an incorrect component concentration of the sample. In addition, according to the present embodiment, the user can comprehend that an analysis result of the sample is obtained by performing measurement in a state where the dispensing probe 1a does not appropriately suck the sample.

Further, according to the present embodiment, a factor of erroneous detection of the liquid level detection and a type of processing to be performed on the sample, etc. (recommended coping procedure) are output to the display unit 9. In this way, the user can refer to the content displayed on the display unit 9 and execute countermeasures from a countermeasure against the factor with a high probability as countermeasures against the factor of the erroneous detection. Therefore, according to the present embodiment, it is possible to reduce the time required for the user to deal with the factor of erroneous detection. That is, it is possible to shorten the time until an abnormal sample is reexamined. In this way, it becomes possible to remove a cause of the erroneous detection from the automatic analyzer 10 at an early stage and restart the operation, so that convenience for the user can be improved.

Further, in the present embodiment, data of an AC signal based on the capacitance between the tip portion 1e of the dispensing probe 1a and the peripheral portion, which is output from an oscillation circuit (for example, CR oscillation circuit 4) used in the capacitance method is stored in the storage unit 6. Further, since the oscillation frequency (waveform) is analyzed based on the data of the AC signal stored in the storage unit 6, there is no need to change the circuit that calculates the capacitance value (for example, the first processing unit 5), and it is possible to perform determination using a separately installed arithmetic processing unit (second processing unit 7). As the second processing unit 7, for example, it is possible to use an operation console such as a PC. This fact means that a condition such as a threshold can be easily changed on software, and the automatic analyzer 10 according to the present embodiment is flexible. Therefore, the automatic analyzer 10 according to the present embodiment is highly practical.

In addition, according to the present embodiment, it is possible to determine erroneous detection of the liquid level detection with high accuracy only by adding the second processing unit 7 and the second controller 8 to the existing automatic analyzer of the capacitance method. For example, when the second processing unit 7 and the second controller 8 are realized by software, the function of the present embodiment can be easily added to the existing automatic analyzer.

Further, a method of processing the liquid level deviation determination by each of the bubble contact determination processing unit 72A and the first liquid level deviation determination processing unit 72B to the fourth liquid level deviation determination processing unit 72E of the second processing unit 7 can be realized using extremely simple calculation formulas (for example, Formulas (1) to (4)), and thus the processing load is small and the time required for arithmetic processing is short.

<Various Modifications>

In the embodiment described above, the liquid level deviation determination and the deviation factor determination of FIG. 5 are performed based on the combination of the five determination results by the bubble contact determination processing unit 72A and the first liquid level deviation determination processing unit 72B (first determination process) to the fourth liquid level deviation determination processing unit 72E (fourth determination process). However, the invention is not limited thereto.

For example, only the bubble contact determination process may be performed without performing the first determination process to the fourth determination process. Further, instead of the first determination process and the second determination process, the bubble contact determination process may be performed.

Further, for example, the liquid level deviation determination and the deviation factor determination may be performed based on a combination of two or more of the five determination results of the bubble contact determination process and the first determination process to the fourth determination process.

For example, the first determination process to the fourth determination process may be first performed, and the bubble contact determination process may be performed when the liquid level deviation determination result by each determination process is 'abnormal', and the deviation factor is determined to be 'bubble' or 'unclear (N/A)'. By performing such a process, it is possible to improve the determination accuracy of erroneous detection when the liquid level deviation factor is the bubble.

Further, for example, a combination to be used may be determined from the bubble contact determination process and the first determination process to the fourth determination process in accordance with the deviation factor to be determined. For example, since the bubble and static electricity are characteristic factors, the determination may be made by a combination of the third determination process and the fourth determination process. Alternatively, the liquid level deviation determination and the deviation factor determination may be performed by combining the third determination process and the fourth determination process with another determination process. When the combination of determination processes (determination results) used is changed in this way, the contents of the liquid level deviation and deviation factor determination table 41 are changed accordingly.

In addition, in both the first determination process and the second determination process, a differentiation operation is performed and determination is performed based on a data series of a differential value. Since processes similar to each other are included, one of the determination processes may be used or both the determination processes may be aggregated.

In addition, a directivity of the third determination process is different from that of the first determination process to the third determination process from a viewpoint that a shape of a capacitance waveform is viewed in a time width greater than or equal to a certain time corresponding to the threshold W. Therefore, it is desirable to include at least the determination result of the third determination process in the combination of determination results. In this way, combinations of determination results are diversified, and the accuracy of the deviation factor is increased.

In addition, in the above-described embodiment, there is a considered method of extracting an average value or a maximum value instead of extracting a minimum value for each certain number of points (certain section) of the time-series data of the capacitance value (detected as the oscillation frequency) as the feature amount.

Further, in the above-described embodiment, when the feature amount is extracted for each certain number of points, the points may not be obtained at equal intervals in time. In other words, even in the method of extracting the minimum value, etc. for each certain number of points or for each certain time region from data sampled each time at variable and appropriate time intervals, the detection performance does not change in principle (that is, the determination result is not affected).

In addition, in the above-described embodiment, when it is determined that erroneous liquid level detection has been performed, the user may be notified using a method of sounding an alarm through a speaker, a method of displaying a warning message on the screen, or a method of adding a mark to a measurement result on the screen, etc.

Furthermore, the invention is not limited to the above-described embodiment, and various other application examples and modifications can be taken without departing from the gist of the invention described in the claims.

For example, the above-described embodiment example is a detailed and specific description of the configuration of the device (automatic analyzer) for describing the invention in an easy-to-understand manner, and the invention is not limited to the one having all the configurations described.

In addition, each of the configurations, functions, processing units, etc. may be realized using hardware, for example, by designing some or all of the configurations, functions, processing units, etc. using an integrated circuit. In addition, each of the configurations, functions, etc. may be realized using software by a processor interpreting and executing a program that realizes each function. Information about a program, a table, and a file, etc. realizing each function can be stored in a recording device such as a memory, a hard disk, or a solid state drive (SSD), or a recording medium such as an IC card, an SD card, or a DVD.

In addition, control lines, information lines, etc. indicated by solid lines in FIG. 1 are considered necessary for description, and it may not be necessary to indicate all the control lines or the information lines on the product. In practice, it may be considered that almost all the components are connected to each other.

Further, in this specification, a processing step describing time-series processing naturally includes processing performed in time series according to a described order and additionally includes processing which may not be performed in time series and is executed in parallel or individually (for example, parallel processing or processing by an object).

What is claimed is:

1. An automatic analyzer comprising:
   a container, the container containing a liquid;
   a dispensing unit that has a dispensing probe and is configured to move a tip portion of the dispensing probe to a liquid level of the liquid in the container and suck and discharge the liquid;
   a housing;
   an oscillation circuit connected to the dispensing probe, the oscillation circuit configured to output an alternating current (AC) signal of an oscillation frequency according to a capacitance between the tip of the dispensing probe and a ground of the housing;
   a detector configured to receive the AC signal of the oscillation frequency output by the oscillation circuit and detect whether the tip of the dispensing probe has come into contact with the liquid level in the container based on the oscillation frequency of the AC signal output from the oscillation circuit;
   a first processing unit comprising a first controller configured to control an operation of the dispensing unit based on a detection result of the detector;
   a feature amount value extraction unit configured to divide time-series data of the oscillation frequency of the AC signal output by the oscillation circuit into a plurality of sections until a certain time elapses after the dispensing probe starts to be lowered for each section of the plurality of sections, extract a feature amount value for each section of the plurality of sections, and output the extracted feature amount value as a data series;
   a bubble contact determination processing unit configured to compute a correlation between a waveform of the data series of the feature amount value output from the feature amount value extraction unit and a waveform model based on a waveform observed when the tip of the dispensing probe comes into contact with a bubble on the liquid level in the container, and determine whether liquid level detection has been performed one way based on a result of computing the correlation; and
   a second processing unit comprising a second controller configured to determine a deviation between the tip of the dispensing probe and the liquid level in the container and a factor of the deviation based on a determination result of the bubble contact determination processing unit;
   wherein
   the feature amount value is a first value and/or second value for each section of the plurality of sections;
   the waveform model corresponds to a trapezoidal waveform having continuous peak values in a section of the plurality of sections corresponding to a number of milliseconds;
   a waveform of a data series of the feature amount value for which a correlation with the waveform model is computed is the waveform of the data series in which a feature amount value extracted by the feature amount value extraction unit before the detector determines that the tip of the dispensing probe has come into contact with the liquid level in the container is deleted from the data series of the feature amount value.

2. The automatic analyzer according to claim 1, further comprising:
   a first determination processing unit configured to compute a differential value of the feature amount value for each section of the plurality of sections of the time-series data of the oscillation frequency, compute a correlation between a second waveform of a data series of the differential value and a corresponding second waveform, and determine whether the liquid level detection has been normally performed the one way from a computation result;
   a second determination processing unit configured to compute a differential value of the feature amount value for each section of the plurality of sections of the time-series data of the oscillation frequency, compare the first value of a data series of the differential value with a threshold, and determine whether the liquid level detection has been performed the one way from a comparison result;
   a third determination processing unit configured to compute a first section of the plurality of sections of the time series data in which a feature amount value for each section of the first section of the plurality of sections extracted from the time-series data of the oscillation frequency satisfies a predetermined condition, compare a length of the first section of the plurality of sections of the time series data with a threshold, and determine whether the liquid level detection has been performed the one way from a comparison result; and
   a fourth determination processing unit configured to compute a value of each data series from a data series of a first value and a data series of a second value as the feature amount value for each section of the plurality of sections extracted from the time-series data of the oscillation frequency, compare a difference between the first value of each respective data series with a threshold, and determine whether the liquid level detection has been performed the one way from a comparison result,
   wherein the second controller is configured to determine a deviation between the tip of the dispensing probe and the liquid level in the container and determine the factor of the deviation by a combination of two or more determination results among determination results by the bubble contact determination processing unit and each determination processing unit of the first determination processing unit to the fourth determination processing unit.

3. The automatic analyzer according to claim 1, wherein the second controller is configured to determine a factor corresponding to one of a bubble generated on the liquid level, a contact or static electricity between the tip of the dispensing probe and an inner wall of the container, or an unclear factor, as the factor of the deviation.

4. The automatic analyzer according to claim 1, wherein the second controller is configured to perform a control operation to output a determination result of the deviation between the tip of the dispensing probe and the liquid level in the container and a determination result for the factor of the deviation to a display unit.

* * * * *

UNITED STATES PATENT AND TRADEMARK OFFICE
CERTIFICATE OF CORRECTION

PATENT NO. : 11,635,444 B2  
APPLICATION NO. : 16/737233  
DATED : April 25, 2023  
INVENTOR(S) : Tsuyoshi Yaita Page 1 of 1

It is certified that error appears in the above-identified patent and that said Letters Patent is hereby corrected as shown below:

In the Claims

Column 25, Line 12, Claim 1, after "tip" delete "portion"

Column 26, Line 12, Claim 2, after "been" delete "normally"

Signed and Sealed this  
Eleventh Day of July, 2023

Katherine Kelly Vidal  
*Director of the United States Patent and Trademark Office*